United States Patent [19]

Smith

[11] Patent Number: 5,720,963
[45] Date of Patent: *Feb. 24, 1998

[54] BARRIER DISRUPTION TREATMENTS FOR STRUCTURALLY DETERIORATED SKIN

[75] Inventor: Walter P. Smith, New Canaan, Conn.

[73] Assignee: Mary Kay Inc., Dallas, Tex.

[*] Notice: The term of this patent shall not extend beyond the expiration date of Pat. No. 5,587,396.

[21] Appl. No.: 544,713

[22] Filed: Oct. 18, 1995

Related U.S. Application Data

[63] Continuation-in-part of Ser. No. 296,513, Aug. 26, 1994, Pat. No. 5,587,396.

[51] Int. Cl.$^6$ ........................................ A61K 7/48
[52] U.S. Cl. ................ 424/401; 424/443; 514/844; 514/846
[58] Field of Search ............... 424/401, 443; 514/844, 846

[56] References Cited

U.S. PATENT DOCUMENTS

| | | | |
|---|---|---|---|
| 4,363,815 | 12/1982 | Yu et al. | 424/642 |
| 5,051,449 | 9/1991 | Kligman | 514/559 |
| 5,091,171 | 2/1992 | Yu et al. | 424/642 |
| 5,190,876 | 3/1993 | Merril, Jr. et al. | |
| 5,215,759 | 6/1993 | Mausner | 424/489 |
| 5,382,432 | 1/1995 | McCook | 424/401 |
| 5,391,373 | 2/1995 | Mausner | 424/401 |
| 5,401,517 | 3/1995 | Meyers et al. | 424/401 |
| 5,422,370 | 6/1995 | Yu et al. | 514/557 |
| 5,476,661 | 12/1995 | Pillai et al. | 424/401 |
| 5,587,396 | 12/1996 | Smith | 514/557 |

FOREIGN PATENT DOCUMENTS

| | | |
|---|---|---|
| 587288 | 3/1994 | European Pat. Off. |
| 9406440 | 3/1994 | WIPO. |
| 9503028 | 2/1995 | WIPO. |
| 9503032 | 2/1995 | WIPO. |
| 9714403 | 4/1997 | WIPO. |
| 9714412 | 4/1997 | WIPO. |

OTHER PUBLICATIONS

Imokawa et al. In J. Soc. Cosmet. Chem 40, 273–285, Oct. 1989.

Soap, Cosmetics, Chemical Specialties, vol. 69, No. 2, Feb. 1993, New York, pp. 20–24, "New ingredients and formulations are cropping up in cosmeceuticals and treatment products for the skin".

Merck Index, element edition, Merck & Co., Inc. 1989, monograph number 87.

"Comparison of Methods for Measurement of Transepidermal Water Loss" by A. O. Barel et al, from *Non–Invasive Methods and th Skin*, pp. 179–184, CRC Press, Boca Raton, Florida 1995.

Mitsushiro Denda, Peter M. Elias et al. "Epidermal injury vs. barrier disruption as initiators of epidermal proliferation and inflammation", from *The Journal of Investigative Dermatology*, vol. 104, No. 4, p. 563 Abstract No. 46 (Apr. 1995).

Pinnagoda et al. "Measurement of the Transepidermal Water Loss" pp. 173–178, chapter 9.1 from Non–Invasive Methods and the Skin, editors J. Serup and G.B.E. Jemec, CRC Press, Boca Raton, Florida 1995.

Barel et al. "Comparison of Methods for Measurement of Transepidermal Water Loss", chapter 9.2 from Non–Invasive Methods and the Skin, editors J. Serup and G.R.E. Jemec, CRC Press, Boca Raton, Florida 1995.

Proksch et al. in "Barrier function regulates epidermal lipid and DNA synthesis" *British Journal of Dermatology* (1993) 128, 473–482.

Rieger et al. "Skin Consitutuents as Cosmetic Ingredients' from Cosmetics & Toiletries", vol. 107, pp. 85–94 (Nov. 1992).

*Primary Examiner*—Jyothsan Venkat
*Attorney, Agent, or Firm*—Finngegan, Henderson, Farabow, Garrett & Dunner

[57] ABSTRACT

New topically applied treatments for structurally deteriorated or otherwise aged skin are shown by comparative data to effect structural improvements in the deteriorated skin, as shown by skin-thickening data. The disclosed treatments disrupt the skin's water barrier and elevate trans-epidermal moisture loss (TEML) for extended periods of weeks or months and include methods of mechanical or solvent action, for example, tape stripping, or acetone washes. Preferred treatments use cosmetic creams or gels with active ingredients such as lactic acid as a primary, water-soluble barrier disruption agent, a retinoid, for example vitamin A palmitate as a lipid-soluble barrier disruption agent and a particular cerebroside to inhibit barrier repair. Such novel creams or gels can be applied daily for extended periods to provide chronic, sustained disruption of the barrier as indicated by significantly elevated TEML. Novel cosmetic formulations have particular application to improving the appearance and structure of sensitive facial areas of the skin.

21 Claims, No Drawings ically deteriorated skin, which will be understood to include skin that is deteriorated by aging and other causes as described above.

BARRIER DISRUPTION TREATMENTS FOR STRUCTURALLY DETERIORATED SKIN

CROSS-REFERENCE TO A RELATED APPLICATION

This application is a continuation-in-part of my U.S. patent application Ser. No. 08/296,513, Aug. 26, 1994 now a U.S. Pat. No. 5,587,396, hereinafter referenced as the "parent application", the disclosure of which is hereby incorporated herein by reference thereto.

TECHNICAL FIELD

The present invention relates to topically applied treatments for deteriorated skin which will stimulate improvements in the appearance and structure of the skin. Deteriorated skin is skin which, as a result of aging, chronological aging, photoaging or both, inadequate or inappropriate nutrition, poor subcutaneous tissue structure or microvasculature, which may be aggravated by lack of exercise, or of other such factors, lacks the structure and attractive appearance of healthy youthful skin. There is an extensive market for cosmetic and pharmacological products as well as salon treatments intended to reduce the ravages of aging and weathering on the skin and to improve its appearance and structure. An ultimate goal of workers in the field is to provide commercial treatments that will quickly restore a youthful complexion without provoking undesirable side effects. The present invention provides a new approach toward that goal.

BACKGROUND

Skin Deteriorated by Aging.

Skin ages naturally with the passing of the years. Aging is accelerated by the action of the sun, which process is known as photo-aging and also by exposure to wind, salt and so on. With aging, skin acquires or exhibits any of a variety of problems including lines, wrinkles, lack of firmness and elasticity, a rough, non-homogeneous stratum corneum, age spots and actinic keratosis.

Other Types of Deteriorated Skin.

Various other conditions are often associated with declines or deficiencies in skin structure or appearance that qualify the skin to be described as deteriorated, for example cellulite manifestations, where a pronounced thinning of the skin and subcutaneous tissue disorders are common, and burn or scar tissue.

Skin Treatments.

Cosmetics that temporarily enhance the skin's appearance by masking irregularities with an opaque cosmetic film or coating have been used for thousands of years. Treatments that will actually improve the quality and appearance of naked, unadorned skin rather than merely masking it have also been known or attempted since ancient times. Treatments employing fruit or milk acids, or vinegar rinses, if maintained consistently for long periods have probably succeeded in warding off some of the visual effects of aging. In recent years effective treatments have been discovered for the rigors of aged skin and a large and growing market exists for products and services that are effective in providing structural improvements in the appearance of aged skin.

One class of products that provide structural improvements to the skin are skin renewal acids, notably alpha hydroxy acids and retinoic acids, or their esters. These acids, acidic compounds or esters work either intracellularly or intercellularly to stimulate skin cell proliferation. Some treatments employing skin renewal acids are disclosed in various patents to Yu and Van Scott, including, for example, U.S. Pat. Nos. 4,363,815, 5,091,171 and 5,422,370 and also in my International Patent Publication No. WO 94/06640. Another class of skin-renewal stimulating products are certain retinoids, for example as disclosed in Kligman U.S. Pat. No. 5,051,449.

Skin renewal acids provide some benefits but tend to irritate, are slow to act and users complain of dry skin. According to Rawlings et al. "Improvements in stratum corneum ceramide levels and barrier function following treatment with alpha hydroxy acids" J. of Investigative Dermatology 1102 (4), 1994 page 538, alpha hydroxy acids do not significantly elevate trans-epidermal moisture loss (TEML). As embodied in the teaching of McCook U.S. Pat. No. 5,382,432, it appears that tolerance of skin renewal acids, or at least of alpha hydroxy acids, increases with use.

A particularly low irritation treatment employing a novel combination of lactic and salicylic acids is disclosed in my International patent application publication No. WO/94/06640

As described in the parent application, a cellulite condition which comprises an unsightly, often embarrassing and sometimes painful lumpiness of the skin, notably in the areas of the thighs, buttocks and stomach, can be described in terms of the following skin and tissue disorders:

I) disrupted fat metabolism and distribution;

ii) poor blood circulation and microvascular distribution;

iii) a thinned out epidermis; and iv) a thinned and inactive dermis with abnormal accumulation of reticular protein around fat cell dumps.

Although both cellulite and aged skin conditions are associated with dermal anomalies, cellulite and aging have not been regarded as related conditions, subject to common treatments. The ill effects of aging exhibit themselves primarily in terms of surface appearances and the disposition of the layers of the skin itself which becomes stretched and loose, whereas cellulite is primarily a sub-dermal phenomenon clearly involving conformational disturbances of the tissues beneath the skin. Aging symptoms are most prevalent on the exposed skin surfaces of the face, neck and hands, whereas cellulite afflicts body regions that are for the most part covered. There is no apparent connection between conventional cellulite treatments involving exercise or non-aerobic and sweating treatments, massage, or aminophylline or caffeine treatments or the like, and known aged skin treatments.

Although convenient for consumer use, cosmetic formulations of skin-renewal acids do not adequately meet the needs of the marketplace for structurally deteriorated skin treatments: they are not suitable for salon application, because of the necessary frequency of treatment; greater potency or efficacy would be desirable, yet greater potency is hard to obtain without increased irritation or other undesirable side effects. Greater potency requires the use of very high concentrations of acids which can be quite irritating and may even require professional supervision for safe use. Another problem in developing treatments for structurally deteriorated skin is the lack of an economical and convenient test for their efficacy: evaluations of possible new treatments must await the outcome of months of application to multiple subjects before reliable data can be obtained and may be depend upon unreliable qualitative judgments or else require elaborate and expensive biophysical determinations.

SUMMARY OF THE INVENTION

The invention, as claimed, is intended to provide a remedy. It solves the problem of providing treatments for structurally deteriorated skin, for example aged skin which treatments are easily applied and quickly effective, and do not cause serious side effects. The invention provides a new approach to the treatment of structurally deteriorated skin which offers providers of skin treatments a wide range of possible treatments from which to choose one which will suit the preferences of any particular individual.

Accordingly, the invention provides a treatment for structurally deteriorated skin comprising repeated topical application of a barrier disruption treatment effective to provide chronic and significant disruption of the skin's water barrier. The chronic disruption is maintained for a long enough period to induce structural improvements in the skin. The water barrier that is disrupted is the natural barrier to the diffusion or evaporation of water vapor through the solid portion of the skin, and does not relate to sweating. The degree and effectiveness of the resultant barrier disruption can be measured by matting determinations of trans-epidermal moisture loss (TEML) on subjects undergoing treatment. Effective treatments significantly elevate TEML long before structural or superficial improvements in the skin become discernible. TEML elevations can be observed within one or two days or a week of the application of the novel aged skin treatment. TEML determinations are made a least one, or preferably at least three hours after a treatment.

Many different treatments can be employed to achieve the desired structural improvements in the skin so long as they are capable of chronically disrupting the water barrier and elevating TEML, in accordance with this invention, without inducing unacceptable side effects such as excessive irritation. Preferably, the treatment is selected and conducted so that TEML is elevated by at least 50 percent. Suitable treatments include tape stripping and solvent stripping but a more preferred treatment comprises topical application of a cosmetic composition containing biologically active substances to disrupt the barrier and elevate TEML.

Since the skin acts rapidly to repair a disrupted barrier, TEML elevations can be difficult to sustain. To overcome this difficulty the present invention introduces the concept of a barrier repair inhibitor as a novel and valuable adjunct to the practice of the invention. Small, biologically effective quantities of a mixture of cerebrosides 1 and 2 have surprisingly been found to inhibit the repair of a disrupted barrier, in spite of the fact that similar quantities have the opposite effect on normal or healthy skin, and actually enhance the barrier.

In another aspect the invention provides an aged or deteriorated skin treatment composition which comprises a primary barrier disruption agent or TEML elevator that is effective to raise immediate or short-term TEML levels accompanied by a supplemental barrier disruption agent that functions to sustain the elevated TEML levels. Preferably, the primary barrier disruption agent is at least moderately soluble in water and the supplemental barrier disruption agent is at least moderately lipid soluble. The supplemental barrier disruption agent can be a cell renewal modulator or accelerator cell differentiation modulator which is effective to sustain the skin repair processes over time, for example a lipid soluble active agent such as a retinoid. Preferably also, as stated above, a barrier repair inhibitor is included in the treatment compositions to prevent premature rebuilding of the water barrier and enhance the composition's aged skin treatment efficacy.

Clinical tests I have conducted, involving in vivo studies of human responses to diverse topical treatments, details of which are reported below, show a quite unexpected beneficial interaction between a primary barrier disruption agent, in this case an alpha hydroxy acid, lactic acid and a supplemental barrier disruption agent, in this case a retinoid, vitamin A palmitate leading to sustained elevation of TEML, that increases with continued application, and is very significantly higher than was obtained with lactic acid alone. Pursuant to the teachings of this invention, this effect is valuable in the long-term treatment of structural skin disorders, including skin deterioration attributable to aging. Used alone, in conventional concentrations for facial application, neither alpha hydroxy acids nor retinoids appear capable of producing adequate barrier disruption and TEML elevation.

Other skin renewal stimulating alpha hydroxy acids, and their equivalents, when used in combination with other dermally effective retinoids and their equivalents are expected to yield comparable results.

To obtain the desired skin improvements, it is also preferred that the skin treatment be carded out for at least eight weeks so that the subject's TEML is elevated by at least fifty percent during and until or after eight weeks of repeated treatments More preferably, the treatment is continued for at least four further weeks and typically, for at least twenty-six weeks or longer to provide an elevation of TEML in excess of 100 percent.

Elevation of trans-epidermal moisture loss can be used to monitor barrier function. When TEML levels are measured after twelve weeks of treatment, taking measurements at least eight hours after application of the last treatment, I have found that known skin treatments, other than retinoids have little, if any, sustained impact on barrier function and some appear to depress TEML levels. Judged by the behaviors of retinoic acid and at least one other exfoliant, in clinical determinations I have made, retinoids and other exfoliants, show only marginal elevations of TEML at twelve weeks which are not regarded as significant for the purposes of my invention, preferred embodiments of which achieve elevations of TEML of at least one hundred percent.

My clinical tests have also shown that aged skin treatments according to the invention have excellent efficacy and can yield valuable structural skin improvements such as thickening of the dermal and epidermal layers of the skin and an improved appearance. Surprisingly, irritation was not reported as a problem by subjects of the tests even although relatively severe treatments were repeated daily for several weeks. As compared with the abilities of known treatments to stimulate structural skin improvements, superior results were obtained.

DETAILED DESCRIPTION OF THE PREFERRED EMBODIMENTS

Overview

Preferred embodiments of this invention employ methods or materials that provoke a chronic and substantial loss of skin water-barrier function to induce the release of factors in the skin that, in essence initiate a skin repair process. When its barrier function is disrupted, the skin responds as though wounded and begins a generalized repair process increasing epidermal and dermal metabolism and angiogenesis, or blood vessel formation, under the control of as yet undefined skin signals released upon barrier disruption.

Unlike cellulite treatments which are generally too severe to be applied to sensitive skin areas, preferred embodiments of the present invention comprise repeated application of a barrier disruption treatment to facial or other sensitive structurally deteriorated skin areas to induce chronic, significantly elevated trans-epidermal moisture loss for extended periods of time until a desired improvement of the structurally deteriorated skin is achieved. The invention includes treatment compositions specially formulated for extended daily application to sensitive facial and other areas to provide severe barrier disruption substantially without irritation.

Role of the Water Barrier.

I have discovered that the water barrier is a control point, regulating one or more of the skin's growth processes and that by disrupting the water barrier to increase diffusion of moisture through the skin to the ambient air, it is possible to stimulate desirable skin growth processes. Furthermore, the disruption may be managed for optimum results and improvements in the appearance, condition and structure of the skin. By artificially disrupting the water barrier in a controlled manner with suitable topical treatments, the thickness of the epidermis can be increased without incurring unacceptable side effects.

It appears from clinical studies conducted pursuant to my invention that a chronic or sustained elevation of trans-epidermal moisture loss triggers release of basal cell growth factors. This is most surprising because other workers in the field have reported, only shortly before the date of this application, that, in murine studies, manipulations that injure the epidermis, namely repeated barrier disruption by topical acetone treatment or tape stripping, lead to cutaneous pathology, or a disease-like condition of the skin, independent of barrier repair. Mitsuhiro Denda, Peter M. Elias et al. in "EPIDERMAL INJURY VS. BARRIER DISRUPTION AS INITIATORS OF EPIDERMAL PROLIFERATION AND INFLAMMATION." *The Journal of Investigative Dermatology*, vol. 104, No. 4, page 563 Abstract No. 46 (April 1995), conclude that the changes induced by acetone treatment or tape stripping appear to be linked to epidermal injury rather than barrier homeostasis or the natural tendency of the barrier to return to a stable condition in response to disruption. This work suggests that the barrier cannot be manipulated to trigger desirable processes.

Prior to my invention, conventional wisdom has held that skin health is fostered by maintaining or enhancing the water barrier by applying barrier creams and the like to coat the skin with a hydrophobic film, for example of mineral oil or petroleum. It is general knowledge that a healthy skin is well hydrated, has a cool, smooth, feel, and is not rough and dry so that sealing in moisture to keep it that way appears to be a reasonable idea, yet I have found that, by disrupting the barrier chronically, for extended periods, rather than attempting to supplement or seal it, structural improvements in the deteriorated skin, resembling the characteristics of healthy skin, can be obtained.

To understand this apparent contradiction a possible model, but not a limiting theory, is to consider the sponge-like characteristics of a healthy skin. Although prone to superficial dryness, the skin is actually supplied internally from an essentially unlimited volume of water and moisture by the blood, lymph and other fluid systems, which supply is ultimately replenishable by drinking. A healthy, resilient skin absorbs and holds moisture from this unlimited supply. Moisture lost to evaporation from the outer surface is readily replenished from internal supplies. The rate of evaporation does not materially affect the water saturation of the dermal tissues. Occluding the outer surface of the skin with a hydrophobic seal may soothe and relieve superficial dryness, but will not significantly affect the saturation and water content of resilient dermal layers of healthy skin that are able to replenish themselves from internal moisture reservoirs.

By contrast, badly deteriorated or aged skin is unable to hold moisture and remain firm. No amount of external occlusion with petrolatum, mineral oil or the like will change this condition. Treatments that stimulate structural improvements are required.

Frequency, Intensity and Duration of Treatment.

The treatments of the invention are carried out with a frequency and intensity and for a duration sufficient to produce the desired result, namely a significant and satisfactory improvement in skin appearance and skin structure, without inducing unacceptable side effects such as excessive or painful irritation or persistent reddening or inflammation. Prior to my invention, workers have not known that a controlled disruption of the skin's water barrier, when artificially induced and sustained for a period of weeks will eventually yield significant structural skin improvements.

Observations made during the course of developing the data reported hereinbelow, indicate that known barrier disruption treatments such as vigorous massage, the use of abrasive sponges (BUFF-PUFF, trademark), and exfoliative granules, although they may temporarily increase TEML, for a few minutes or hours after application, do not sustain such effects. Pursuant to my invention the elevation of TEML necessary to achieve desired structural improvements in the skin and the repair of damage to aged skin must be chronic and sustained, which has not been achieved by the conventional practice of such treatments.

Similarly, exfoliant treatments such as facial peels (for example, 20–30% lactic or glycolic acid or equivalent), in single applications, or repeated at intervals, such as weekly, although they may increase TEML for several days after treatment, do not achieve the desired skin repair effects. Again, pursuant to the concepts of this invention, these deficiencies are believed to be due to a failure of the treatment to provide a sustained elevated rate of TEML over an extended course of treatment, for example, lasting at least eight weeks.

A professional worker, or a subject of the treatment, can control the frequency or duration of the treatment by monitoring the treatment's progress and side effects. In general terms, the most aggressive treatment that does not produce unacceptable discomfort nor obvious reddening that persists, nor inflammation, will be most effective. Frequency is controlled by convenience: few people will wish to apply, or receive a treatment more than twice a day. The skin's sensitivity and recovery rate, as indicated by irritation or pathological indicators such as reddening or inflammation, may also influence frequency.

As stated above, the degree of barrier disruption can be monitored by determining TEML. Treatments, or treatment parameters, that produce the greatest elevation of TEML, without unacceptable side effects, are preferred. The treatments of the invention are relatively long-term treatments and it is chronic or long-term elevation of TEML that is desired to produce structural improvements in aged or otherwise deteriorated skin.

The barrier has natural homeostatic properties meaning that like most biological organisms it quickly responds to injury to repair the damage. As a living organism, the barrier naturally tends to counteract changes that threaten its host's survival. Thus, the skin quickly responds to barrier disruption and elevated TEML by repairing the barrier and returning TEML to normal levels. Because of this responsiveness, temporary TEML elevations, with a duration less than one hour, are not significant to the practice of this invention.

What is important is to provide a significant elevation of TEML, when measured some hours after application of the treatment, which is still present when the treatment has been under way for several weeks. Such a belated showing of TEML elevation may be taken as an indication that TEML has been chronically raised on a sustained basis throughout the treatment, providing constant stimulation of desirable skin repair processes.

Quite significant elevation of TEML is desired. While an elevation of 50 to 70 percent may be adequate to yield useful benefits, an elevation of at least 100 percent is preferred. More preferably, the TEML elevation lies in the range of from about two times normal to about four times normal. Elevations as high as about 8–10 times normal are indicative of complete removal of the stratum corneum leading to reddening and super-sensitivity and are accordingly undesirable and are certainly to maintain for a prolonged period of weeks or months. Some users may be able to tolerate elevations between four and eight time normal, especially if there normal TEML is low, so that a practical limit is about six times normal.

A limitation on the TEML obtained may be skin or surrounding tissue sensitivity. Thus, in the eye area, which is critically important to a user's facial appearance, the skin, and of course the eye itself, are acutely sensitive and treatments for this and other sensitive areas which provide lower TEML rates may be preferred by users, for example elevations below 150 percent and perhaps in the range of 50 to 100 percent. Results will be slower coming but treatments will be easier, or more comfortable to apply. The disruption of the barrier and increase in TEML can result in a temporary increase in skin dryness, a minor side effect. Such dryness typically reaches a peak after two or three weeks of treatment and thereafter is improved.

Clearly, the aggressiveness of the inventive treatments must be controlled to be tolerable over periods of weeks or months without causing severe or painful irritation, reddening, peeling or excessive discomfort. However, minor manifestations of these symptoms may be tolerable by many people for short periods of time.

General Nature of the Novel Treatments.

Properly applied, effective treatments may be mechanical or chemical or physico-chemical and include treatments such as solvent or detergent stripping which can remove lipids from the stratum corneum barrier as well as tape stripping or abrasive treatments which can physically destroy or remove the barrier. One or another of the foregoing treatments may be selected by an individual and performed under professional supervision in a salon, but none provides a commercially appealing over-the-counter preparation. Also, difficulties may be encountered in applying these treatments to the face, and especially to eye areas.

To meet these needs, the invention also provides a cosmetic composition suitable for repeated topical application which includes an effective quantity of a chemically or biochemically active barrier disruption agent to provide the desired barrier disruption and TEML elevation. While many substances, or combinations of substances, can induce the barrier disruption uniquely desired by the present invention, a combination of ingredients that has been found to provide a particularly effective barrier disruption agent comprises an alpha hydroxy acid and a retinoid or, for better stability and shelf life, a retinoic acid ester. The alpha hydroxy acid is preferably in a free state, and the composition is preferably significantly acidic. The alpha hydroxy acid is believed to provide an initial elevation of TEML which is prolonged by cell-proliferation stimulating and, perhaps, differentiation modulation properties of the retinoid.

The treatments of my invention are relatively severe, more severe than would conventionally be regarded as advisable for daily or twice daily application to sensitive skin areas, especially the face, for extended periods, yet in clinical tests of embodiments of my invention subjects have reported surprisingly little irritation.

Since the skin responds to elevated TEML by rapidly repairing the damaged or disrupted water vapor barrier, an inhibitor of this barrier repair response is preferably also included in the treatment composition. I have found that certain cerebrosides, notably cerebrosides 1 and 2, are particularly good barrier repair inhibitors. This finding is surprising in view of the apparent role of ceramides, structural precursors of cerebrosides as important barrier components. Ceramides, though structurally related to cerebrosides, are distinctly different compounds from cerebrosides. Cerebrosides are in effect glycosylated ceramides bearing a saccharide moiety coupled to a terminal hydroxyl group of the residual ceramide structure, which ceramide hydroxyl is thereby rendered biologically unavailable. In the skin, cerebrosides are produced in the living basal epidermal cells. They are short lived and are quickly enzymatically converted to ceramides.

Screening Method.

The invention also provides a novel method of screening topical treatment compositions for efficacy in stimulating structural skin improvements, which method comprises applying a prospective treatment to a subject repeatedly at intervals, for example twice daily, matting TEML determinations on the subject at least three, or preferably at least six hours after a treatment and selecting a treatment showing significant abilities to induce chronic barrier disruption, as indicated, for example by a substantially elevated TEML, elevated by perhaps 100 percent or higher, after some weeks of treatment, e.g. eight or twelve weeks. TEML measurements are simpler and less expensive than biophysical determinations of structural changes in the skin, moreover, it appears that significant increases in TEML, are reliable and earlier indicators of treatments capable of inducing structural improvements. It should be noted that immediate increases in TEML, such as might be induced by a simple alcohol rub, that endure for a few minutes or at most one hour, are not what is to be measured. TEML measurements are made after the barrier has had time to make a normal recovery from transient damage, for example at least two hours after a treatment, and preferably six or more hours afterwards.

Cellulite Treatments of the Parent Application.

The parent application disclosed and claimed topical treatments for cellulite-afflicted skin which succeeded in providing significant structural improvements in both the skin and the cellulite condition. These improvements were obtained by a variety of treatments which provide a sustained and elevated trans-epidermal moisture loss ("TEML") referenced as trans-epidermal water loss "TEWL" in the parent, which is indicative of a continued disruption of the skin's water barrier and of a failure adequately to repair that barrier. The degree and duration of barrier disruption taught in the parent application were not known prior to that invention. To the best of my belief, prior therapeutic cosmetic or dermatological treatments have not used elevation of TEML levels as a useful treatment parameter serving as a guideline as to the efficacy of a particular treatment on a given subject prior to the invention of my parent application. Conventional skin care treatments, and indeed conventional skin care wisdom, aim to supplement barrier function and reduce TEML. Many cosmetic moisturizers have used humectants such as glycerine, sodium PCA, or hydrophobic occlusive agents, such as petrolatum or mineral oil to lower TEML rates and trap water in the skin for a transitory and superficial improvement in skin appearance.

The TEML levels referenced in the parent application relate to passive diffusion of water vapor through the stratum corneum and do not include sweating. When collecting the clinical data reported in the parent application, to ensure that there was no sweat gland activity, subjects were preconditioned at a controlled temperature and controlled relative humidity, as described in more detail hereinbelow. Cellulite treatments according to the teachings of the parent application are capable of improving any or all of the four problem conditions described above, namely disrupted fat metabolism, poor blood circulation, thinned-out epidermis, and abnormal protein accumulation around fat cell clumps.

Thus, the barrier disruption treatments of the parent application attack not only the subcutaneous tissue and blood vessel disorders associated with the fat cell accumulation problems that are characteristic of cellulite manifestations, but they also attack the structural skin disorders which accompany cellulite afflictions, leading to structural skin improvements, as disclosed in my parent application, which skin improvements may be of value anywhere on the body whether or not cellulite is present.

In the light of the present invention, it follows that the treatments of the parent application can be employed for the purpose of treating relatively insensitive skin areas that are deteriorated, but not necessarily cellulite-afflicted.

Summary of Broad Teaching.

In summary, the present invention is based on the discovery that any one of a variety of novel topical treatments either chemical or physical in nature, which chronically alters the homeostasis of the skin barrier has the unexpected result of significantly and appreciably improving the structure of disordered skin and of modifying the function of the skin. Such treatments may comprise continual, regularly repeated aggressive treatments that disrupt the skin barrier sufficiently severely that the TEML is significantly, or preferably dramatically elevated on a sustained basis. Such treatments can be managed to deliver surprisingly effective changes in the appearance of the skin which are consistent with and may be perceived by subjects or onlookers as providing a rejuvenating effect. This is particularly surprising since conventional teachings indicate that barrier disruption will affect the skin but that the effect will not be beneficial and will be inflammatory: carried over a long period of time (months) constantly induced inflammation would result in severe negative effects or even a pathological condition.

Whereas other workers have regarded the skin barrier as a structure whose integrity should be maintained, if skin condition is to be enhanced, I have found that by managed disruption of the skin barrier, as described herein and in the parent application, surprisingly favorable results can be obtained, apparently because sustained or chronic elevation of the level of TEML stimulates skin reconstruction processes that have not hithertofore been accessible to commercially marketable treatments.

Prior to my invention, workers skilled in the art have believed disruption of the skin barrier to be undesirable and have believed that chronic disruption of the barrier would result in negative skin conditions such, for example, as dryness and irritation. While some of the treatments described herein may produce dryness, the effect is minor and not sustained. Irritation need not be a problem.

Psoriasis is recognized as a manifestation of a process involving chronic disruption of the barrier and is suggestive of the sort of condition that a typical skilled worker has expected would develop as a result of chronic alteration of the stratum corneum barrier. The fact that many or most cosmetic and dermatological preparations include one or more lipid materials intended to repair or maintain the skin barrier bears witness to this belief. As previously stated, many cosmetic products have been developed with the sole purpose of reducing TEML. The present invention does the opposite and elevates TEML.

Overcoming the Difficulty of Barrier Repair.

There are difficulties in disrupting the skin barrier in a sustained manner arising not only from the need to avoid excessive irritation or more serious damage, but also from the skin's natural ability to effect quick repairs when the barrier is damaged. For these reasons, to the best of my knowledge, prior topical cosmetic or dermatological treatments have not resulted in sustained or chronic alteration of the homeostasis of the stratum corneum. Nor have prior treatments resulted in significant or elevated elevation of TEML levels when these are measured at two or more hours after the treatment.

I have also discovered that the natural processes the skin employs rapidly to repair a disrupted barrier can be inhibited by including in a topical treatment according to the invention a suitable biologically active agent. To find such an agent which would be acceptable for inclusion in commercial products without incurring regulatory difficulties, I investigated various biologically active skin lipids and found, surprisingly, that of the materials studied, cerebrosides 1 and 2 were effective whereas closely related cerebroside 3 was not. Nor were ceramides nor sphingosine effective.

Topical Treatments

As stated above, the present invention provides methods of topical treatment of deteriorated or aged skin as well as cosmetic topical treatment compositions. In preferred embodiments, these treatments and treatment compositions disrupt the skin barrier function, with a 200 to 300 percent or greater increase in TEML levels, and treatments are applied to maintain this increase continually and chronically over at least an 8-week period and preferably beyond that period to 26 weeks or such other time as a satisfactory improvement in the skin's condition is obtained, for example for 10 to 20 weeks.

The desired TEML increases can be obtained by sustained treatments with suitable chemical compositions or mechanical disruption methods or solvent extraction, provided the treatments are sufficiently aggressive to disrupt the skin water barrier. Important to the invention is to increase TEML while maintaining a low, tolerable, irritation level since caustic chemicals used to disrupt the barrier, solvents used to extract lipids, and surfactants can all be very irritating.

Thus, barrier disruption treatments that can be used in the practice of this invention include direct physico-chemical destruction of the lipid structure of the stratum corneum by a dermatologically tolerable organic solvent for low molecular weight lipids, such as acetone or by a dermatologically tolerably surfactant, for example sodium lauryl sulfate. Such treatments detach and remove barrier-component lipids. Preferred, however is the use of a topically applied cosmetic composition, containing chemically active barrier disruption ingredients in an aesthetically attractive, non-odorous formulation such as a cream for absorption into the skin. Other suitable barrier disruption treatments will be known or apparent to those skilled in the art.

Some suitable chemical or biochemical compositions that may be used in cosmetic composition treatments according to the invention include, but are not limited to, chemical exfoliative compositions such as alpha hydroxy acids, retinoids and combinations thereof, proteases such as pronase, papain, trypsin and the like applied at concentrations, frequencies and for durations effective to provide the desired improvements in skin characteristics.

Some mechanical exfoliative materials include but are not limited to nylon polyethylene, and other synthetic particulate beads. Natural particulate organic materials such as crushed organic matter, for example apricot pits, and natural abrasive implements such as sponges, may also be used.

Other physical means of perturbing the stratum corneum and disrupting the water barrier can also be effective, for example, stripping the skin with adhesive tape, or cyanoacrylate adhesive, or paraffin wax. Another class of barrier disruption treatments effective to increase TEML comprises physical-chemical means which act by removing barrier lipids from the stratum corneum, thus increasing TEML. Organic solvents such as hexane, acetone or methanol and strong detergents such as sodium lauryl sulfate do not physically remove layers of the stratum corneum, but are effective in elevating TEML, because they disrupt the water vapor barrier by removing significant lipid materials from the stratum corneum.

One preferred deteriorated or aged skin treatment composition according to the invention comprises an exfoliative, for example an alpha hydroxy acid, in an effective proportion as a primary barrier disruption agent, combined with a retinoid, or retinoid equivalent, in an effective proportion as a secondary disruption agent. While such a composition can provide desired levels of TEML elevation in excess of 50 percent, it is strongly preferred to include an active concentration of a specific cerebroside substance or material, or equivalent barrier repair inhibitor. The alpha hydroxy acid and retinoid together provide a surprisingly effective TEML elevator and the cerebroside substance or material is selected to inhibit barrier repair and prolong TEML elevation. The composition should not be physically occlusive in the sense of impeding moisture egress through the stratum corneum by coating or impregnating it with occlusive materials such as lipids, nor should the composition include biochemically active substances that impede the action of the cerebroside, permitting rapid or normal barrier repair. My experimental data suggest that free fatty acids and cholesterol exhibit this undesirable property and should therefore be excluded from the skin treatment compositions of the invention. Triglycerides and other compounds containing esterified fatty acids which may decompose and release free fatty acids in the composition should also be avoided.

A preferred alpha hydroxy acid is lactic acid at a concentration of about 3 percent and a moderately acid pH of from about 3.5 to about 5.0. Salicylic acid, a beta hydroxy acid, can also be used, for example, at a concentration of about 2 percent and a pH of about 3. Other exfoliants that can be used include mechanical exfoliants such as scrubbing granules or proteolytic enzymes, which work by removing thin outer cell layers of the stratum corneum.

A preferred retinoid cell wall stimulate which can be combined with the lactic acid, salicylic acid or other exfoliant is retinyl palmitate, or vitamin A palmitate, in a proportion for use on sensitive areas such as facial areas, of about 0.1 to about 0.5 percent, for example, about 0.3%.

The cerebroside is preferably a mixture of cerebrosides 1 and 2, for example from a natural extract such as a bovine extract, and a preferred proportion is from about 0.01 to 2.0 percent, more preferably about 0.1 to 1.0 percent. Proportions of about 0.3 to about 0.5 percent are suitable for use with stronger barrier disruption formulations intended for less sensitive areas such as the limbs and trunk, while higher concentrations, for example from 0.6 to 1.0 percent are desirable for facial and other sensitive areas where less strong barrier disruption formulations are apparently desirable to reduce the risk of irritation.

Conceivably, the cerebroside mixture can be a synthetic mixture if the individual cerebrosides 1 or 2 are available in a suitably pure form, or the individual cerebrosides 1 or 2 may be used. Other cerebrosides such as cerebrosides 3 through 6 do not appear to be effective and are not intended for use in practicing this invention.

Materials to be avoided because they may interfere with the effectiveness of the aged skin treatment composition by lowering TEML, below what the compositions of the invention can otherwise achieve, are occlusive materials, especially lipids, or biological actives that assist barrier repair or impede the action of barrier repair inhibitors, for example phospholipids, sphingosine, free fatty acids, cholesterol and more traditional cosmetic lipids, for example mineral oil, emollients and the like.

Some other materials which can be used, in combination with an effective concentration of a barrier repair inhibitor such as about 0.1 to 1.0 percent of cerebrosides I and 2, to provide effective aged skin treatments according to the invention, are a strong detergent such as an aqueous or hydroalcoholic solution of sodium lauryl sulfate which detergent should preferably be combined with an ingredient to inhibit primary irritation, for example, green tea extract. Where the hydroalcoholic solvent is predominantly alcoholic, for example about 70 percent ethanol, the proportion of detergent may be lower, for example about 1 percent.

Another combination of ingredients that can be combined with a barrier repair inhibitor, being applied either together therewith or in a separate step, is an alpha hydroxy acid, such as 3% lactic acid, combined with an effective proportion of abrasive or exfoliative particles, for example about 5% of crushed apricot pits or polyethylene or nylon spheres, together with a suspension agent or gelling agent, for example a carbomer such as CARBOPOL 940 (trademark Goodrich) in a proportion of about 0.2 percent by weight. Such an abrasive and exfoliative composition preferably is adjusted to a rather strongly acid pH of about 3.0 and, preferably also, anti-irritants are included, as described elsewhere herein.

Many of the materials or techniques employed in these treatments have previously been used at home, or in salons as dermatological therapies or as beauty treatments or are known to the cosmetic arts. However, to the best of applicant's belief, prior to the present invention, none has been used to an extent and in a manner such as to obtain an acutely and chronically elevated TEML, achieving sufficiently high levels for a sufficiently long period to indicate a sustained disruption of barrier function such as I have discovered will stimulate structural improvements in the skin. Nor has any prior treatment known to me employed a barrier repair inhibitor in conjunction with one or more barrier disruption agents to promote skin improvements via a sustained, chronic and significant elevation of TEML. In particular, none has used selected cerebrosides as barrier repair inhibitors and prior workers have not known of the unique barrier repair inhibition characteristics of a mixture of cerebrosides 1 and 2.

Thus, prior treatments have not been practiced in a manner consistent with the stimulation of prolonged and maintained structural skin repair processes that are achieved by the method of this invention which leads to measurable benefits such as thickening of the skin as well as general improvements in the appearance of the skin and specific reductions in unsightly blemishes such as fine lines, keratosis and melanin spots. Thus, prior art treatments have not been used in a manner consistent with nor sustained at a level or duration sufficient to induce a daily and extended increase in TEML indicative of barrier dysfunction.

Lactic Acid and Vitamin A Compositions

In practicing a particularly preferred embodiment of this invention, I have discovered that a combination of unbuffered lactic acid, an example of an alpha hydroxy acid, used at relatively strong concentrations, together with vitamin A palmitate or alcohol, synergistically increases TEML. The alpha hydroxy acid disrupts the skin's water barrier and quickly, or immediately elevates TEML in minutes or hours. It appears that vitamin A palmitate, a retinoid, supplements and promotes that TEML elevation in the longer term over days or more probably one or two weeks, providing a striking enhancement of the TEML elevation. These TEML-stimulating properties may be attributable to the effects of retinoids on skin cell differentiation and proliferation. This is a different mechanism from the above-described treatments which act directly on the barrier to disrupt the lipid bi-layer, to remove lipids by solvent extraction or remove the barrier by direct or mechanical exfoliation.

The result of the interaction of vitamin A palmitate with lactic acid is quite unexpected. While such a combination, at relatively high strengths, of an alpha hydroxy acid and a retinoid provides valuable elevations of TEML, much more valuable long-term elevation and skin improvement properties are obtained by including in the topical treatment composition a barrier repair inhibitor, such as a cerebroside 1 and 2 mixture, as is described above.

Preferred embodiments of the invention when applied topically to the skin are believed to exfoliate the skin chronically and severely so as to induce extensive cell loss and more importantly so as to disrupt normal barrier functions whereby TEML is increased preferably as much as 200 to 300 percent. Although physical means can be used to achieve these effects, as described above, it is a discovery of this invention that from about 5 to about 10% unbuffered lactic acid and 0.1%–3.0% vitamin A palmitate achieves this result reproducibly with modest irritation. A combination of 6% lactic acid and 0.5% vitamin A palmitate, was found to be particularly effective. Chronic high rates of TEML are believed to induce the release of critical skin growth factors such as interleukins and transforming growth factors resulting in a stimulation of dermis-epidermis growth and an angiogenic effect. Such treatments may be too severe for use on facial skin, but on thigh, arm and breast areas, the skin is more resistant. Treatment with the above composition thickens and improves the dermis and epidermis while the angiogenic effects improve long-term blood flow promoting the health and condition of the skin.

Barrier Repair Inhibition.

Because the skin responds rapidly to repair any damage to the barrier, as a survival measure, to induce elevated TEML levels that endure for prolonged periods, the invention employs a barrier repair inhibitor to slow the natural repair processes. The employment of measures to restrain or impede the natural barrier repair processes is an important feature of this invention. Barrier repair inhibition promotes attainment of the desired structural improvements in the skin by facilitating the maintenance of elevated TEML levels without requiting subjects to suffer severe irritation or to tolerate prolonged or frequently repeated treatments.

Natural barrier repair involves synthesis and release of hydrophobic lipid material components of the barrier and a proper physical organization in the lipomembrane. Inhibition may imply suppressing such lipid synthesis and release, or it may imply impeding proper assembly of the lipid fabric of the barrier. In optional embodiments of this invention, such synthesis is inhibited to reduce the availability of free fatty acids, sphingolipids and cholesterol for barrier repair, for example by topical application of a specific cerebroside.

As disclosed hereinabove, a natural mixture of cerebrosides 1 and 2 has been found to be a particularly effective barrier repair inhibitor, but other materials such as structural analogs of cerebrosides 1 and 2, or of the individual cerebrosides, and functional equivalents thereof, are contemplated as having utility in the practice of the invention. Such materials and possible mechanisms of barrier repair inhibition are discussed more fully hereinbelow.

Cerebrosides for use in the practice of the invention are commercially available in several forms. They are sometimes supplied as glycosphingolipids (GSL) which term includes any lipid with a sphingosine group linked to a sugar. As supplied, cerebrosides are a principle component of GSL which are somewhat crude biological isolates from plants or animals. A relatively pure (99%) mixture of Types 1 and 2 bovine brain cerebrosides is available from Sigma Chemical Co., catalog number C 4905. This source is free of significant quantities of cholesterol or free fatty acid, which appear to interfere with the barrier repair inhibition properties of cerebrosides 1 and 2. Other cerebroside materials are available from a number of commercial vendors including Centerchem, Inc., Plantech Inc., Natural and Marine Resources, Inc. but should be purified of interfering contaminants such as cholesterol, free fatty acids and the like, prior to use.

In view of the role of natural lipids as barrier repair materials, preferred embodiments of the invention avoid applying free fatty acids, cholesterol or equivalent lipid materials or other water-vapor occlusive materials which could reduce desired TEML levels by occluding and thus temporarily repairing an otherwise disrupted and impaired barrier. Cellularly active substances which may stimulate liberation of lipids or other barrier building materials, for example, substances such as sphingosine, are also avoided.

Should the topical treatment of the invention comprise removal or washing away of skin lipids with a lipid solvent, then such a lipid synthesis inhibitor is applied in a separate step from barrier disruption. Where barrier disruption is effected by topically absorbed active agents, a lipid synthesis inhibitor can be included in the formulation.

Such use of a lipid synthesis inhibitor as a barrier disruption inhibitor can prevent rapid regeneration of the water barrier and provide enhanced structural improvements in the skin or better efficacy of the treatment process.

Relative Proportions of Ingredients

Suitable relative proportions for formulating the ingredients of the inventive compositions as topical applications for sale in cosmetic or medicament emollient, lotion or tonic formulations, and their application rates, are described hereinbelow. A preferred cosmetic formulation is a cream suitable for daily massaging, or simply spreading and rubbing, by the consumer. Other such quantitative parameters that can be used to obtain the benefits of this invention will be apparent to those skilled in the art.

A limit on the strength of the skin treatment compositions of the invention is the degree of irritation they may induce. Depending upon its potency and irritability, a useful proportion of a simple, biochemically acting, TEML elevator, for example an alpha hydroxy carboxylic acid, for incorporation in a topical treatment composition is from about 1 to about 15 by weight of the composition.

Different areas of the skin have different sensitivities and the proportion of barrier disruption agent or agents should be varied accordingly to avoid excessive irritation. Thus, sensitive areas like the face and neck are preferably treated with a lower concentration within the range, for example from about 1 to about 6 percent by weight alpha hydroxy acid, more preferably about 2 to about 4 percent, and less sensitive areas like the hands, arms, legs, chest or abdomen can receive stronger concentrations in the middle of the range, for example from about 5 to about 10 percent of an alpha hydroxy acid for example lactic or glycolic acid or of salicylic acid.

Where a retinoid is employed to assist the barrier disruption function by accelerating cell renewal, a useful proportion is from about 0.005 to about 6.0 percent by weight, with from about 0.1 to 3.0 percent being preferred and proportions in the range of from 0.3 to 1.5 percent being particularly preferred. For less sensitive limb and trunk areas, higher proportions in a range of from about 0.5 to 6.0 percent by weight, preferably about 1.0 to 2.0 percent, can be used whereas lower concentrations in a range of from about 0.1 to 0.5 percent by weight are preferred for sensitive facial areas and other sensitive areas such as the neck.

When a specific cerebroside or a specific cerebroside mixture is used as a barrier repair inhibitor of the invention, a useful proportion is from about 0.01 to about 5 percent with a range of from about 0.05 to about 1 percent being preferred and of from about 0.1 to about 0.5 percent being particularly preferred.

Unless otherwise stated, or apparent from the context weight based on the total by weight based on the total weight of the composition and refer to the proportion of active ingredient or its equivalent.

PH of Treatment Compositions

Depending upon the acidity of the TEML elevator a preferred pH is somewhat acidic, and indeed sustained moderate, but tolerable, acidity is believed to promote barrier disruption. Accordingly a preferred pH is in the range of about 3.0 to 6.2 with 3.5 to 5.5 being more preferred. Low pH's indicate greater acidity, which is more irritating.

Optional Ingredients

Some useful optional additional ingredients that can be incorporated individually or in combination one with another, in aged skin treatment compositions according to the invention are primary anti-irritants and anti-oxidants, which counter immediate irritation, preferably at concentrations known to be effective in topical cosmetics, for example from about 0.5 to 7.0 percent by weight, individually, and more preferably about 1 to 3 percent, as well as conventional additives such as fragrances and colorants. Moisturizers and such customary additives may be included so long as they are not materials with significant water-vapor occlusive properties, or barrier enhancement properties, as described hereinabove.

Anti-irritants and antioxidants can be used to optimize tolerance of sustained, elevated TEML. Examples of suitable anti-irritants are kola extract, green tea, aloe, and the like and examples of suitable anti-oxidants are BHT, NDGA, vitamins E and C, and propyl gallate.

Application Rates and Frequencies

Rates and frequencies of application are chosen to provide desired elevations of TEML on a sustained basis to stimulate the structural skin improvements described herein.

Typical application rates of relatively simple biochemically active substances, for example substances that appear to act intercellularly, (between or externally of the cells), such as alpha hydroxy acids, the novel aged skin treatment compositions described herein can range from about 0.01 to 0.5 mg of active acid ingredients per square centimeter of skin, where the acid is a low-molecular weight hydrophilic acid, such as an alpha hydroxy carboxylic acid, with a range of from 0.05 to 0.2 mg/cm$^2$ being preferred. Liquid phase cosmetics are generally applied at rates of about 2–3 mg/cm$^2$. With an active ingredient proportion of about 0.15 to about 30 weight percent, this gives a possible rate of application of active ingredients of from about 0.003 mg/cm$^2$ to 0.9 mg/cm$^2$. A preferred range is from about 0.01 to 0.5 mg/cm$^2$, with a range of from 0.05 to 0.2 mg/cm$^2$ active ingredient per unit skin area being more preferred.

This dosage is applied to whatever skin area requires treatment, preferably once or twice a day. More frequent applications of three or four times a day are likely to be wasteful of product without providing additional benefits, whereas less frequent applications, notably once a day, result in reduced efficacy. Additional applications may occasionally be made after washing, bathing or swimming, up to a maximum of about six times a day.

Alternative Barrier Disruption Treatments

As an alternative to disrupting the water barrier with a combination of an alpha hydroxy acid and a retinoid, TEML can be increased via mechanical methods, for example stratum corneum stripping with adhesive tape, or physicochemical methods, for example, solvent extraction, or other methods which provide sustained or chronic elevations of TEML, to the extent described herein, without unacceptable irritation or damage.

Solvent Extraction with Acetone.

Daily, or every other day, rinses with acetone have also been found to disrupt the skin's water barrier, when continued over a long period of time, for example, two months. Biophysical measurements suggest that such an acetone rinsing regimen should deliver the above-described long-term skin-repair effects. Acetone will remove lipids as they are forming and interfere with barrier repair. Acetone is however, strongly irritating, flammable, and noxious and is not recommended for use. Data such as that reported in Table 4 below, help confirm that the broad scope of the concepts of the invention is not limited to application of cosmetic compositions to disrupt the skin water barrier and elevate TEML but extends to other, physical and physicochemical treatments.

Tape Stripping.

Stripping the skin 5–10 times with adhesive-coated cellophane tape is another effective barrier disruption method which can be carried out once or twice daily to increase TEML 2 to 10 times, depending upon an individual subject's particular response. More severe treatments can be carried out less frequently, for example, every second or third day, using an aggressive adhesive such as a cyanoacrylate adhesive attached to a suitable support.

Over an 8-week period such tape stripping treatments can induce positive biological effects consistent with structural improvements in the skin. Positive results with this treatment further confirm the broad technical scope of the invention. However, tape stripping has numerous drawbacks for use as a commercial process including but not limited to the fact that responses to tape stripping vary widely with different individuals, and an expensive, lab instrument must be used to monitor barrier function.

Surfactant Stripping.

It has also been discovered that a strong aqueous surfactant solution used on a daily basis can disrupt the barrier chronically. A surfactant such as 10% sodium lauryl sulfate (SLS) applied twice a day is sufficient. Used alone, SLS is irritating to use over an 8-week period. Addition of anti-irritants, or antioxidants may effectively control or reduce long-term irritation so that the treatment is considered mild enough to use as a practical embodiment of the invention.

If desired, any of these mechanical or physico-chemical non-cream barrier disruption treatments, which are effective to elevate TEML, can be accompanied by topical application of a cream containing a retinoid and, optionally, a cerebroside, to augment and prolong TEML elevation and skin repair processes.

Trans-Epidermal Moisture Loss (TEML)

TEML and its Determination.

Pursuant to the present invention, TEML measurements were made on subjects of various skin treatments including both conventional treatments and novel treatments some, though not all, of which are treatments constituted in accordance with the present invention. Various indicators of structural improvements were also measured and comparative clinical gradings of induced irritation, were made.

Some known methods of determining trans-epidermal water loss are described in Pinnagoda et al. "Measurement of the Transepidermal Water Loss" pp. 173–178 and Barel et al. "Comparison of Methods for Measurement of Transepidermal Water Loss", chapters 9.1 and 9.2 of "Non-Invasive Methods and the Skin" editors J. Serup and G. B. E. Jemec, CRC Press, Boca Raton, Florida 1995. These authors use the abbreviation "TEWL" for transepidermal water loss. The abbreviation "TEML is used herein for transepidermal moisture loss to emphasize that steps are taken to ensure that water loss through the sweat glands is excluded.

As used in this application, the term "TEML" refers to evaporative water losses due to a constant flux of water vapor through the solid portion of the stratum corneum. TEML does not include sweating, and subjects of the tests reported below were conditioned to ensure that sweat was not a factor when TEML measurements were taken. TEML is maintained at a normal low level by the presence of certain lipids having an organized structure in the outer layers of the stratum corneum. The stratum corneum is the outermost integral structure of the skin and is usually regarded as a living component, though some workers might disagree. A few layers of dead skin cells are usually loosely adhered to the stratum corneum and easily removed by nothing more dramatic than scrubbing. Removal of the stratum corneum, or of the lipid-containing outer layers of the stratum corneum, or removal of the lipids from those layers disturbs and elevates TEML. This phenomenon is quite distinct from sweating which is a discharge of sweat stored in the sweat glands beneath the stratum corneum through capillary passages which extend through the stratum corneum.

Standard operating procedure at a good research laboratory requires subjects for such studies to be equilibrated for 30 minutes prior to skin measurements at a standard temperature of 20° C. and a relative humidity of about 40 to 50% while seated and relaxing.

Such procedures were followed in obtaining the TEML data reported below. Subjects were not allowed to drink coffee or caffeinated beverages so that there was minimal sweating and the bulk of the measurement, and of any changes, could be attributed to barrier function and not to sweating.

As a further safeguard to exclude the effects of sweating, skin temperature measurements were taken prior to testing and if skin temperature was above 31° C. or below 27° C., measurements were not taken.

An EVAPORIMETER (trademark SERVO-MED) measuring instrument was used for TEML determinations. This equipment comprises a moisture-collection chamber which occludes a skin surface area. The instrument detects moisture-dependent conductance and TEML levels are read when steady state conditions are reached. Subjects are pre-conditioned at a temperature of about 68°–71° C. of and a relative humidity of about 30–40%. The instrument employed for the tests described below had a sensitivity of about ±1.0%, although the day-to-day variability of an individual subject's skin is somewhat higher than this even under controlled conditions. These procedures are designed to ensure, inter alia that subjects are neither sweating nor perspiring and that discharge of sweat does not participate in the TEML determinations. Thus, the TEML determinations are a measure of water vapor passing the stratum corneum by passive diffusion.

In the clinical experiments reported below, protocols involving determination of TEML levels at skin areas receiving topically applied skin treatments employed a procedure in which each treatment tested was applied twice daily and a TEML determination was made a short time prior to a morning application. For example, in many cases, the treatment was applied at about 10 a.m. and about 6 to 8 p.m. while the TEML determination was made about 9 a.m., approximately one hour prior to the morning application and at least eight, or more probably twelve, hours after the evening application.

Determination of Other Parameters

Skin Thickness Determinations

An effective technique for measuring skin thickness is by ultrasound imaging which can detect changes in subcutaneous fat, blood vessel distribution and epidermal and dermal integrity. Skin thickness can be measured by a computer analysis of such skin ultrasound scans. One such instrument is a CORTEX Dermascan C instrument, which was used to obtain the skin thickness data in the experiments reported hereinbelow. Ultrasound scans provide a non-invasive way to make objective and accurate determinations of epidermal and dermal thickness. Increases in dermal and epidermal thickness are important indications of an improved and healthier skin structure attributable to the growth of new skin layers and usually accompanied by an improved, more youthful appearance.

Determination of Irritation

Irritation was evaluated by comparative chromaticity determinations of skin color, by industry standard methods, employing a Minolta Chroma Meter, Minolta Camera Co. Ltd. Additional subjective perceptions of stinging, burning and skin redness after application were recorded, and the data were combined into a clinical irritation index having a scale of from 0 to 5 on which 0 indicates no discernible or reported irritation, and 5 indicates severe irritation.

Clinical Experiments with Prior Art Skin Treatments

The results of clinical experiments with two prior art skin treatments are reported in Table 1 below. The prior art actives in Table 1 were applied twice a day for the duration of the study.

For treatment 1.1 RETIN A (trademark) was supplied at a concentration of 0.5% in a simple cream base. Exfoliation for treatment 1.2 was a mechanical exfoliation with 5% polyethylene beads suspended in a carbopol gel, vigorously applied and rinsed off twice a day.

TABLE 1

Experimental Data:
Evaluation of Conventional Skin Treatments

| Treatment | Blood flow | TEML g/mc/hr | Skin thickness epidermal increase | Irritation Grade |
|---|---|---|---|---|
| 1.1) RETIN A* 0.5% | | | | |
| baseline | 1 | 2.17 | x | 1 |
| 8 wks | x | x | x | 2 |
| 12 wks | 1.27 | 2.37 | 4% | 2.5 |
| 1.2) EXFOLIATION | | | | |
| baseline | 1 | 2.41 | x | 1 |
| 8 wks | x | x | x | 1.5 |
| 12 wks | 1.07 | 2.17 | ns | 2.25 |

*Trademark of Johnson & Johnson Co. for retinoic acid. ns = not significant

Referring to the blood flow data in the first column of Table 1, treatment 1.1 with retinoic acid shows some significant improvement in basal blood flow, while treatment 1.2, exfoliation, shows a slight, but not significant, elevation of blood flow. As will be described, inventive treatments can attain blood flow elevations in excess of 40%. Such blood flow improvements are associated with material improvements in skin structure, as shown by qualitative and quantitative data reported hereinbelow.

The blood flow increases reported in Table 1 are not immediate and temporary effects attributable to irritation induced by the applied product. Measurements were taken 8–12 hours after product application and reflect an increased blood flow rate into the skin after about 8 or 12 weeks of treatment, as reported. The beneficial results are attributable to epidermal and dermal stimulation by the applied product, resulting in new blood vessel growth.

Referring to the TEML levels in Table 1 and comparing the levels at twelve weeks with the baseline levels, it can be seen that Treatment 1.1, using retinoic acid, produced a very modest elevation of TEML, of only about 10%, far short of the significant elevation of at least 50 percent required by the present invention. The mechanical exfoliation treatment 1.2 actually depressed TEML It may be concluded that neither of these relatively severe treatments was effective as a barrier disruption treatment which would induce significant elevation of TEML.

As reported in the third column of data, only insignificant improvements in skin thickness were shown by the prior art skin treatment compositions of Table 1.

Both skin treatments resulted in a progressively increasing grade of irritation with the passage of time, as reported in the last column of Table 1.

Neither significant elevation of TEML nor significant improvement in skin thickness, a fundamental structural indicator of tissue health, was obtained with either prior art treatment, clearly showing the shortcomings of the prior art. Although the invention is not limited by any particular theory, it appears that prior art treatments do not provide a sufficiently sustained disruption of the skin's water barrier function to stimulate significant skin repair.

Tape Stripping Tests.

Various skin lipids were evaluated for their role in improving the barrier of healthy skin by determining the number of tape strips required to obtain a 200% elevation of TEML (to a level approximately three times its normal value) determining TEML as described elsewhere herein, on the morning after the treatment. Tape stripping was performed as described above and the results are reported in Table 2.

Cosmetic Vehicle for Tests

A simple gel-forming cosmetic vehicle capable of solubilizing small quantities of lipid actives or comparatives for use in the tests described hereinbelow can be formulated as follows:

| Cosmetic vehicle for tests (proportions by weight) | |
|---|---|
| ethanol SD40 | 10.0 |
| carbomer gelling agent | 0.2 |
| CARBOPOL 941 (trademark B. F. Goodrich Co. | |
| ethoxydiglycol solubilizer | 10.0 |
| TRANSCUTOL (trademark Gattefosse) | |
| actives or comparatives | as reported in Tables 2–3 below |
| water | Q.S. to 100.0 |

The pH is adjusted to about 6.0 except where otherwise indicated or appropriate, for example, where lactic acid is an active.

TABLE 2

Experimental Data:
Role of cerebrosides in improving the barrier of healthy skin

| Treatment applies to healthy skin | No. of tape strips required for 200% elevation of TEML |
|---|---|
| no treatment | 6.7 |
| 0.3% cerebrosides 1 & 2 | 11.9 |
| 0.3% cerebrosides 3 | 12.3 |
| 0.3% phospholipids | 7.3 |

Referring to Table 2, it may be seen that cerebrosides, without discrimination, as between a mixture of cerebrosides 1 & 2, and cerebroside 3, display significant barrier enhancement properties when applied to normal skin, in the light of which their ability to inhibit the repair of a disrupted barrier is truly surprising. Thus whereas untreated normal skin required merely 6.7 strips for 200% TEML elevation, and a phospholipid treatment made little difference (7.3 strips), 75% or more strips (11.9 or 12.3) were required to induce sufficient barrier disruption to obtain a 200% TEML elevation after treatment with a cerebroside.

Thus, the Table 2 data suggest that the cerebrosides tested have barrier-enhancing properties when applied topically to normal skin.

Surprisingly, in the light of the Table 2 data showing significant enhancement of the barrier of normal skin, I have found that when a treatment comprising small quantities of a mixture of cerebrosides 1 & 2 along with an alpha hydroxy acid and a retinoid, is applied to skin having a barrier disrupted by tape stripping, to a TEML elevation of at least 200%, repair of the barrier is significantly inhibited. This barrier inhibition phenomenon is illustrated by the data described in Table 3 below, which reports the time taken for TEML levels to return to normal, which is to say approximately to the levels recorded prior to stripping. After tape stripping, different treatments comprising the cosmetic vehicle described above with the addition of active or test ingredients as indicated in Table 3 below, were applied to the volar forearms of at least six subjects for each test. TEML determinations were made shortly prior to the morning treatment. The numbers reported are an average of a minimum of six subjects.

TABLE 3

Experimental Data:
Role of cerebrosides in inhibiting barrier repair of skin having a defective barrier produced by stripping
"LA" is lactic acid. "VAP" is vitamin A palmitate.

| Treatment applied to stripped skin | Days until TEML returns to normal |
|---|---|
| 1) no treatment | 4.6 |
| 2) 0.3% cerebrosides 1 & 2 | 3.2 |
| 3) 0.3% cerebrosides 3 + 3.0% LA + 0.3% VAP | 7.8 |
| 4) no cerebrosides + 3.0% LA + 0.3% VAP | 6.1 |
| 5) 0.3% cerebrosides 1 & 2 + 3.0% LA + 0.3% VAP | >20 |
| 6) 0.3% cerebrosides 1 & 2 + 0.3% LA + 0.3% VAP + 0.1% cholesterol + 0.5% free fatty acids | 8.9 |

Referring to Table 3, the data reported show that treatments comprising cerebrosides alone (line 2), or comprising alpha hydroxy acid and retinoid without cerebroside (line 4), or alpha hydroxy acid and retinoid with cerebroside 3 (line 3) provide only a modest inhibition of barrier repair as evidenced by the number of days required for TEML to return to normal, which peaks at 7.8 for any of these compositions. The composition of line 5, containing cerebrosides 1 & 2 along with alpha hydroxy acid and retinoid was dramatically more effective in inhibiting barrier repair, so that TEML still had not returned to normal 20 days after the initial stripping treatment.

Thus, whereas a comparable treatment employing cerebroside 3 delayed the return of normal TEML levels by rather less than 100% as compared with no treatment, (7.8 days versus 4.6 days), showing a modest ability to inhibit barrier repair, which was apparently only in minor part attributable to cerebroside 3 (compare lines 3 and 4), cerebrosides 1 & 2 displayed a potent barrier inhibition function, delaying the return of normal TEML levels by more than 300% (>20 days versus 4.6 days). When small quantities of cholesterol and free fatty acid were added to the most effective barrier inhibition treatment, containing cerebrosides 1 & 2 (that of line 4) the result (line 6) was a striking reduction in the ability to inhibit repair of a damaged barrier. Though both cholesterol and free fatty acids are potentially occlusive agents the quantities employed are too small for occlusive effect. Rather, it appears that cholesterol and free fatty acids interfere with the activity of cerebrosides 1 & 2 at the cellular level. Speculating, it is possible that cholesterol and free fatty acid may form complexes with the cerebrosides, thereby interfering with their activity.

A mixture of cerebrosides 1 & 2, which is a commercially available material, is accordingly particularly valuable for use as a barrier repair inhibition agent in the practice of this invention. As shown by the data reported in line 6 of Table 3, the cerebrosides 1 & 2 should be used in the absence of cholesterol or free fatty acid which may require care in sourcing the cerebroside material, since commercial extracts from biological sources often include cholesterol, free fatty acids and the like. As reported above, Sigma Chemical supplies a high-purity extract of cerebrosides 1 & 2. Biofermentation processes are another source. A limited number of extracts from wheat or hibiscus plants also contain relatively pure mixtures.

I have contemplated other materials that may be useful barrier repair inhibitors, including analogs and homologs of cerebrosides 1 and 2, with a view to identifying materials which would retain those features that confer activity on the active cerebrosides 1 & 2 and distinguish them from cerebrosides 3. Looking at the structures of the corresponding ceramides, as set out by Rieger on page 88, I note that the corresponding ceramide 1 is terminally esterified with linoleic acid and this feature is unique vis-a-vis the other ceramide structures depicted. This linoleic tail may be important for barrier inhibition activity and it may also be that the activity of the commercially available mixture of cerebrosides 1 & 2 is attributable solely to cerebroside 1. This issue could be determined by experiment, given availability of individual cerebrosides 1 and 2. If cerebroside 1 is the sole active cerebroside, then it would appear that analogous or homologous materials for employment in the invention can include those having significant structural correspondence with the linoleic tail of ceramide 1, retaining in particular the conjugated double bond feature of linoleic acid. If cerebroside 2 displays significant barrier inhibition activity, then attention possibly should focus on the presence of the double bond adjacent the two hydroxyl groups in the vicinity of the amide moiety. In the inactive cerebroside 3, this double bond is hydrated, which may perhaps account for the inactivity and such materials are contemplated as being useful in the practice of the invention. The invention extends to analogs, homologs and equivalents of mixed cerebrosides 1 & 2 which have barrier inhibition activity.

While I am not familiar with the extent to which the essential natural structure of cerebroside 1 or 2 may be varied while still providing an adequate, or perhaps even an enhanced barrier repair inhibition properties, the structural considerations described above should be taken into account. Until more is known of what structural characteristics influence cerebroside behavior, it appears that such analogs or homologs should, referring to their corresponding ceramides, retain the double bond and dihydroxy amide structure, although a single methyl substituent in these moieties may not unduly depress activity. Having regard to the inactivity of cerebroside 3, additional polar substituent in this region of the molecule appear undesirable. However so long as a significantly hydroalcoholic, lipid character is retained overall, a hydroxy or oxy substituent in either hydrophobic tail appears acceptable. Additionally, or alternatively, one or more methyl, ethyl, or vinyl groups may be substituted in either tail. The invention embraces such postulated effective analogs and homologs of cerebrosides 1 and 2. Such barrier repair inhibition agents should preferably have good epidermal penetration properties as well as resistance to enzymatic conversion or feedback.

The barrier-disruptive treatments of the invention release signals to the lower levels of the skin to increase synthesis of lipids such as ceramides and repair the barrier. A non-limiting hypothesis of the invention is that application of cerebrosides 1 and 2 may interfere with this synthesis, preventing the barrier from repairing itself. It is possible that a general inhibitor of lipid synthesis, or other end products of skin lipid synthesis, other than cerebrosides 1 and 2, may also be effective supplements to the treatments described above to sustain elevated TEML and thus promote skin repair over an extended period.

In tests not reported here, I have found that closely related skin constituents such as phospholipids, ceramides and sphingosine have minimal effect as barrier repair inhibitors for the purposes of the present invention and I have further found that cerebrosides used alone are not useful in maintaining elevated TEML or providing structural improvements to aged skin. Thus, by incorporating cerebrosides in a topically applied cosmetic composition, along with TEML-elevating materials, lipid metabolism can be inhibited, an elevated TEML can be sustained in chronic manner and structural skin improvements can be obtained without subjecting the user to uncomfortable or disagreeable treatments.

Examples of Aged Skin Treatment Compositions

Some specific examples of deteriorated skin treatments suitable for topical application to the face and other sensitive areas of the skin, will now be described.

EXAMPLE 1

Deteriorated Skin Treatment Suitable for Less Sensitive Body Areas

To provide a cosmetic composition suitable for use on less sensitive body areas, such as the limbs and trunk, the following ingredients are mixed according to the directions given below ("Concn."=concentration and the "Phase" number groups the ingredients for addition at different stages of the mixing process):

| Ingredient | Concn. | Phase |
|---|---|---|
| Cetearyl alcohol (and) ceteareth-20 | 3.00 | 1 |
| GMS-PEG 100 stearate | 3.00 | 1 |
| PEG-100 stearate | 1.75 | 1 |
| dimethicone | 5.25 | 1 |
| capric triglyceride | 3.00 | 1 |
| mineral oil | 8.00 | 1 |
| propylparaben | 0.10 | 1 |
| vitamin A palmitate | 1.00 | 1 |
| water | 45.00 | 2 |
| glycerine | 11.00 | 2 |
| butylene glycol | 6.00 | 2 |
| carbomer 941 | 0.20 | 2 |
| methyl paraben | 0.25 | 2 |
| triethanolamine | 3.10 | 3 |
| lactic acid | 10.00 | 4 |
| cerebrosides 1 & 2 | 0.50 | 5 |
| green tea extract | 5.00 | 6 |
| fragrance | QS | 7 |
| water | QS to 100.00 | — |

Those skilled in the art will be familiar with methods for formulating these ingredients into a smooth cream for topical application. The oil phase (1) is slowly added to phase (2) at 80° C. with mixing. After the resultant emulsion begins to form phase (3) is added and the cream thickens. Next phase (4) is added and phase (5–7) ingredients are added as the cream cools to 55° C. It is then cooled to room temp with mixing.

In this Example it will be apparent that vitamin A palmitate, lactic acid and cerebrosides 1 and 2 are active ingredients according to the invention while the balance of ingredients constitutes a liquid vehicle facilitating application.

Clinical Determinations of the Efficacy of Treatments According to the Invention The results of clinical experiments with novel deteriorated skin treatments are reported in Table 4 below. Treatments 2.1 to 2.4 were conducted using the cream vehicle described in the Example above, with the active ingredients and proportions reported in the Table.

Treatments 2.1 to 2.3 and 2.5 may be novel, but are included for comparative purposes and are not preferred embodiments of the, invention.

TABLE 4

Experimental Data:
Deteriorated skin treatments according to the invention

| Treatment | Blood flow | TEML g/mc/hr | TEML incr. % | Skin thickness increase | Irrit. |
|---|---|---|---|---|---|
| 2.1) 5% lactic acid | | | | | |
| baseline | 1 | 2.07 | | x | 1 |
| 8 wks | x | 2.33 | 13 | x | 1.5 |
| 12 wks | 1.11 | 2.47 | 19 | 7% | 1.5 |
| 2.2) 10% lactic acid | | | | | |
| baseline | 1 | 2.11 | | x | 1 |
| 8 wks | x | 2.69 | 27 | x | 1.5 |
| 12 wks | 1.07 | 2.83 | 34 | 10% | 2 |
| 2.3) 10% LA/1% VAP | | | | | |
| baseline | 1 | 2.03 | | x | 1 |
| 8 wks | x | 3.47 | 71 | x | 2 |
| 12 wks | 1.12 | 3.67 | 81 | 8% | 2.5 |
| 2.4) 10% LA/1% VAP/ 0.5% GSL | | | | | |
| baseline | 1 | 1.91 | | x | 1 |
| 8 wks | x | 3.87 | 102 | x | 2 |
| 12 wks | 1.43 | 6.88 | 260 | 10% | 2.5 |
| 2.5) daily 2x BUFF PUFF ™ | | | | | |
| baseline | 1 | 2.14 | | x | 1 |
| 8 wks | x | 2.39 | 8 | x | 1.5 |
| 12 wks | 1.07 | 2.31 | 8 | ns | 2 |
| 2.6) daily 5–10x stripping | | | | | |
| baseline | 1 | 2.14 | | x | 1 |
| 8 wks | x | 5.37 | 151 | 6% | 2.5 |
| 12 wks | 1.17 | 6.07 | 184 | 10% | 3 |
| 2.7) acetone washes (every 2 days) | | | | | |
| baseline | 1 | 2.17 | | x | 1 |
| 8 2ks | 1.12 | 6.92 | 219 | 6% | 2.75 |
| 12 wks | x | x | x | x | x |

LA = lactic acid. VAP = vitamin A palmitate. GSL = glycophingolipid ns = not significant Referring to Table 2, somewhat greater TEML elevations were obtained with treatments 2.1 and 2.2 employing lactic acid, but even the level for the strong exfoliating 10% lactic acid composition of treatment 2.2 is only about 33% Higher levels are desirable to obtain the benefits of this invention. Treatment 2.3 with vitamin A palmitate added to lactic acid shows a TEML elevation at 8 weeks of about 71% and at 12 weeks of about 81%. Although these elevations of TEML are more substantial than those obtained with known treatments, the inventive barrier disruption treatments 2.4, 2.6 and 2.7 achieve much higher elevations of TEML and ranged from over 100% to as much as 260%. Irritation levels, although elevated somewhat, remained tolerable.

Except for treatment 2.4, employing a preferred combination of topically absorbed ingredients pursuant to the invention, basal blood flow as reported in column 1, showed only a modest response to the tested treatments no more than would be expected from regular massaging. More strikingly, treatment 2.4 shows a much higher basal blood flow increase of about 43% at 12 weeks.

A grading for clinical irritation is shown as a safe guard. Excessively irritating treatments are unacceptable. An irritation grading approaching 3 begins to be undesirable and it may be noted that the acetone wash treatment, treatment 2.7, not surprisingly, shows a significant irritation level of 2.75 at only 8 weeks whereas, the preferred low-irritant embodiment of treatment 2.4 shows an irritation rated at only 2.

While treatments 2.1–2.4 and 2.6 all showed some improvement in skin thickness, the inventive treatments 2.3, 2.4 and 2.6 all were at least as substantial as the comparative treatments, while the preferred 2.4 treatment exhibited thickness increases among the best.

In summary, the data reported in Table 4 show that the inventive treatments 2.3, 2.4, 2.6 and 2.7 provide much greater TEML elevations than comparative treatments and these elevations are accompanied by striking improvement in blood flow not obtained by comparative treatments. The preferred inventive composition of treatment 2.4 shows far and away the best results with marked TEML elevations accompanied by major blood flow improvements and significant skin thickening. The results obtained with the convenient, comfortable and esthetic topical cosmetic formulation of treatment 2.4 were better than or at least as good as any other treatment including the rather drastic tape and solvent stripping method of treatments 2.6 and 2.7.

EXAMPLE 2

Mild Treatment for Deteriorated Skin, Suitable for Facial Application

A milder composition suitable for facial application, but otherwise similar to Example 1 was formulated with following ingredients using the method of Example 1

| Ingredient | Concn. | Phase |
|---|---|---|
| Cetearyl alcohol (and) ceteareth-20 | 3.50 | 1 |
| GMS-PEG 100 stearate | 3.50 | 1 |
| PEG-100 stearate | 2.00 | 1 |
| dimethicone | 5.00 | 1 |
| capric triglyceride | 4.00 | 1 |
| mineral oil | 6.00 | 1 |
| propylparaben | 0.10 | 1 |
| vitamin A palmitate | 1.00 | 1 |
| water | 45.00 | 2 |
| glycerine | 5.00 | 2 |
| butylene glycol | 6.00 | 2 |
| carbomer 941 | 0.20 | 2 |
| methyl paraben | 0.25 | 2 |
| triethanolamine | 3.10 | 3 |
| lactic acid | 5.00 | 4 |
| cerebrosides 1 & 2 | 0.15 | 5 |
| green tea polyphenols | 5.00 | 6 |
| fragrance | QS | 7 |
| water | QS to 100.00 | — |

This composition employs a smaller quantity of lactic acid than used in Example 1 and provides results comparable with those obtained with the composition of Example 1, after allowing some reduction in efficacy for the lower concentration of lactic acid.

Further Primary Barrier Disruption Agents

As described above, in a preferred embodiment of the invention the barrier disruption agent or TEML elevator is a cosmetically compatible, pH-reducing, hydroxy carboxylic acid, preferably with exfoliant properties, and is at least moderately soluble or, preferably, quite soluble in water or a hydroalcoholic vehicle for incorporation into a cosmetic composition.

A preference for at least moderate water solubility of the primary barrier disruption agent and moderate lipid solubility of the supplemental barrier disruption agent has also been stated above. The point of these solubility preferences is to provide a compound barrier disruption agent which can express activity in both polar and non-polar elements of the skin's fabric.

While precise solubility characteristics will vary from patent to patent, suitable limits will be known, or apparent to those skilled in the art, based on the teaching herein. In general terms, the primary barrier disruption agent should be more soluble in water than in a standard solvent for non-polar materials, for example, ether, while the supplemental barrier disruption agent should be more soluble in such a standard organic solvent than it is in water. In general, retinoids are quite soluble in ether and oils and are quite insoluble in water while low molecular weight alpha hydroxy acids such as lactic, glycolic, citric and malic acids are quite soluble in water and substantially insoluble in ether. More specific solubility characteristics are available from the literature.

Suitable acids include alpha hydroxy carboxylic acids, especially for example, lactic acid and glycolic acid, as well as other hydroxy carboxylic acids, for example 2-hydroxybenzoic acids, especially for example, salicylic acid, and topically effective salts or complexes of such acids with an inorganic or organic base, for example, ammonium, sodium or potassium hydroxide or triethanolamine. Such salts or complexes, however, if used are preferably delivered, in an acidic composition, with a pH preferably in a range of about 3.5 to about 5.0. The effectiveness of such acids appears to relate to their ability to reduce the pH of intercellular fluids in the skin. A particular acid to use, and its concentration are selected to obtain a desired TEML elevation without excessive irritation. As disclosed in my International Patent Application WO/94/06640, a particularly effective and low irritant alpha hydroxy acid composition also includes a minor proportion of salicylic acid, for example, an approximately 2:1 mixture of lactic and salicylic acids. Such mixtures can be used as the primary barrier disruption agent herein.

Preferably, the TEML elevator is soluble in water or a somewhat polar hydroalcoholic vehicle to provide an effective solution of the active ingredient for incorporation in cosmetic foundations. Many other alpha hydroxy acids can be used as alternatives to lactic acid. Lactic acid is a particularly preferred TEML elevator in the practice of this invention, having excellent efficacy and being a naturally occurring substance found in skin and intercellular fluids as well as in the bloodstream.

Some preferred alternatives to lactic acid are glycolic acid, salicylic acid and mixtures of these acids.

In order to have desired pH-reducing and TEML-elevating properties as well as cosmetic compatibility and moderate water or hydroalcoholic solubility, preferred hydroxybenzoic acids have a molecular weight below about 250 and preferably below about 175.

As set forth above, many hydroxy carboxylic acids that have skin-renewal stimulating properties are described in my International Patent Application WO 94/06640 which relates to a surprisingly effective yet low-irritant combination of alpha hydroxy and salicylic acids, which combination can be used in practicing the present invention. Any of the hydroxy or keto carboxylic, organic acids, or combinations thereof, disclosed or referenced therein as having useful skin-renewal stimulating properties can be used in the practice of this invention as primary barrier disruption agents. Generally, lower molecule weight acids, below about 200 daltons, are preferred, although the lowest, glycolic acid is excessively irritating. The term "primary" is used because the alpha hydroxy acid is recited first herein and may, function chronologically prior to any supplemental agent, but is not intended to suggest that the primary agent is more important or present in a greater quantity.

Additional alpha hydroxy carboxylic acids, and their equivalents described in the above-cited patents to Yu and Van Scott, including, for example, U.S. Pat. Nos. 4,363,815, 5,091,171 and 5,422,370. The acids and acid equivalents described in. these publications, the disclosures of which are incorporated herein by reference thereto, can be employed in the practice of the present invention if they meet the criteria described above. Preferably, the alpha hydroxy acid used in my inventive composition is a straight or branched chain aliphatic acid with not more than three substituent in the aliphatic backbone, said substituent being non-basic and being selected from the group consisting of hydroxy, aldehyde, keto, carboxyl, chloro and nitro.

While acidity and water or hydroalcoholic solubility are desirable characteristics of the alpha hydroxy acids of the present invention, any extremes of these characteristics, such as would be displayed by a mineral acid, are undesirable as being liable to induce not just irritation but severe clinical conditions such as burning, lesions and subcutaneous penetration. Such undesired characteristics can sometimes be displayed by low molecular weight materials which may exhibit unusual and unpredictable, and often harmful, idiosyncratic behavior Such other alpha hydroxy aliphatic acids that can be used in practicing this invention are preferably monocarboxylic acids selected from the group consisting of 2-hydroxy-n-butanoic acid, 2-hydroxy-isobutanoic, 2-hydroxy-n-pentanoic, 2-hydroxy-isopentanoic, 2-hydroxy-n-hexanoic acid, 2-hydroxy-isohexanoic acid. Di-or polyhydric analogs thereof can also be used, for example, 2, X-dihydroxy analogs thereof where "X" is an integer from 3 to 6, as appropriate for the respective monohydroxy acid, indicating the carbon atom location of a second hydroxyl substituent in a carbon atom other than the one or two carbon atoms. Preferably, such dihydroxy acids balance the additional electronegativity attributable to the second hydroxyl with a further hydrophobic moiety as described above. Some examples of suitable dihydroxy acids are maleic acid, $(CH.COOH)_2$ and azelaic acid $HOOC.(CH_2)_7.COOH$.

Since alpha hydroxy acids do not provide significant chronic or prolonged elevation of TEML, and the skin learns to tolerate them in a matter of a few weeks, in order to prolong and intensify the barrier disruption effect, and obtain a desired sustained elevation of TEML, the hydroxy acid is augmented by a supplemental barrier disruption agent such as a suitable skin-renewal retinoid, as described below.

Further Supplemental Barrier Disruption Agents

In accordance with the invention as described herein, some suitable supplemental barrier disruption agents are lipid-soluble, skin-renewal stimulating retinoids, for example tretinoin, or retinoic acid. As disclosed above, surprisingly, I have found that a combination in a topical composition of a skin renewal alpha hydroxy acid and a skin renewal retinoid can provide an eight-week elevation of TEML which is dramatically higher than simple addition of their effects would produce.

Many retinoids or retinoics are unstable and not suitable for marketing in a cosmetic topical treatment composition. Vitamin A palmitate is a particularly stable retinoid and is therefore preferred for use in this invention. Other stable retinoids suitable for formulating in compositions according to this invention include other retinoic acid esters such as retinyl acetate and retinyl alcohol.

Other retinoids having a stable retinyl group linked to a fatty acid chain providing oil-stability and good solubility in the topical application vehicles described herein, can be used in the inventive compositions. In practicing the methods of the invention, shelf life may not be important. Accordingly, stability of the selected retinoid may be less significant if, for example, topical applications are made up on an as-needed basis and are not stored for long periods, enabling less stable retinoids to be used.

Many active retinoids are known and believed in the practice of the present invention, for example, as listed in Kligman U.S. Pat. No. 5,051,449, the disclosure of which is hereby incorporated herein by reference thereto. Some other such retinoids are vitamin A aldehyde, vitamin A acid, vitamin A esters, isotretinoin, etretinate, acitretin retinoid esters, esters and amides of 13-cis and 13-trans-retinoic acid and retinyl glycosides. In addition, β-carotene-based vitamin A precursor compounds are believed effective, as may be vitamin D-based compounds.

While the invention is provided by the treatments disclosed herein and the valuable results that can be obtained from these treatments, and is not governed by theoretical considerations, nevertheless it may be helpful to theorize as to the causes of the sustained barrier disruption effect, the active barrier disruption agents employed in the practice of this invention can produce. Such theoretical considerations can help an understanding of the invention and can assist those skilled in the art better understand what alternative or equivalent treatments or treatment compositions will or will not be workable.

Thus, it appears that an alpha hydroxy acid is effective, when a suitable acid, concentration and pH are used, to provide a short-lived disruption of the barrier and to stimulate cell proliferation which may eventually provide more sustained barrier disruption as immature cells become incorporated in the stratum corneum. Retinoids will also stimulate cell renewal and can modulate differentiation helping cells to mature. Also, retinoids tend to be lipid soluble and therefore more resistant to biological degradation or metabolism so that they survive longer in the active biological environment of living skin tissues and can be effective over longer periods of time. In contrast, alpha hydroxy acids are rather simple, reactive, water-soluble compounds that may be rapidly buffered, neutralized, esterified or metabolized by natural processes, so that they quickly lose their effect.

For reasons which are not all together clear it may be deduced that the combined effect of the action of these two different types of cell renewal stimulants is a relatively inadequate production of skin lipids, or inadequate maturation of the intercellular skin lipid structure which binds the stratum corneum and comprises the water barrier.

Theorizing further, it appears that chronic barrier disruption, with sustained elevation of TEML, may be attributable to a combination of effects which begin with the alpha hydroxy acid acting macrobiologically to modify the pH and polarity of the outer layers of the skin membrane, reducing hydrophobicity and thus permitting increased moisture diffusion. As shown by McCook, who teaches that increased concentrations of alpha hydroxy acids should be used as treatment progresses, the skin system, in time, perhaps one or two weeks, adapts to these changes, restoring TEML. This phenomenon is verified in subjective reports by alpha hydroxy acid uses of induced dryness during the first week or two of use.

The retinoid presumably acts intracellularly, that is to say within individual cells, to influence protein expression and in combination with the changed environment produced by the alpha hydroxy acid stimulates proliferation and accelerates differentiation whereby the intercellular lipid links, or "mortar", in the outer layers of the stratum corneum that constitute the water barrier are incompletely formed, permitting continued moisture diffusion to the atmosphere.

To obtain these effects, relatively high concentrations of the barrier disruption agents are preferably used. The inventive preference is for a concentration would conventionally would conventionally be regarded as near the maximum for continued daily use of the individual agent on sensitive skin tissues such as the face. Ranges of perhaps two to five percent of alpha hydroxy acid, more preferably about 2.5 to 3.5 percent, are preferred along with about 0.15 to about 0.5 percent of a retinoid, more preferably about 0.25 to about 0.35 percent. Higher proportions of barrier disruption agents, that would conventionally be regarded as too severe for continued daily use, even when employed alone, can be used in formulations intended for less sensitive tissues, such as the limbs or hands.

Further Barrier Repair Inhibitors

As indicated above, cerebrosides have been found to fill a valuable functional role as barrier repair inhibitors for the purposes of this invention. This role is believed to be achieved by inhibiting the synthesis of lipids whose incorporation in the stratum corneum provides normal water barrier functions. In keeping with this concept, other substances are contemplated as filling the desired barrier repair inhibition role.

Such barrier repair inhibition enables the elevation of long-term eight- or twelve-week TEML levels to be substantially intensified.

As disclosed herein, a preferred barrier repair lipid synthesis inhibitor is a specific cerebroside, and I have found a mixture of cerebrosides 1 and 2, to be particularly effective. As taught by Proksch et al. in "Barrier function regulates epidermal lipid and DNA synthesis" British Journal of Dermatology (1993) 128, 473–482, murine studies show that disruption of barrier function results in an increase in the synthesis of free fatty acids, sphingolipids and cholesterol in the living layers of the epidermis, leading to barrier repair, at least in mice.

It appears probable that as the biology of the skin's barrier repair processes is better understood, other barrier repair inhibitors will be found. One possible example is an inhibitor of the deglycolysase enzyme which converts cerebrosides to ceramides. Such an enzyme inhibitor would produce an accumulation of cerebroside. Such a deglycolysase inhibitor is believed to exist naturally as a result of a genetic defect which is associated with an accumulation of cerebrosides in a serious medical disorder, Gaucher's disease. It is possible that cerebroside inhibition may have to be more specific, and directed to controlling deglycolysase activity on only those cerebrosides that are active barrier repair inhibitors, possibly only cerebrosides 1 and 2 or an effective one of those two cerebrosides, if the deglycolysase enzyme is that specific.

It is also possible that synthetic or natural analogs and homologs of cerebroside 1 and cerebroside 2 may have comparable barrier repair inhibitory activity.

With regard to their chemistry and biochemistry cerebrosides are themselves generally regarded as skin lipids, being glycosylated ceramides, or to use another description, condensation products of a sphingosine with a carboxylic acid and a sugar. Typically, the cerebroside molecule contains aliphatic chains of sufficient length to give the molecule significantly hydrophobic, or non-polar characteristics although their glycosylation renders cerebrosides significantly less polar than the corresponding ceramides which are deglycosylated. Unlike ceramides, cerebrosides do not appear to be significant structural constituents of the barrier. The structural characteristics of, and differences between, ceramides and cerebrosides are described in Rieger et al. "Skin Constituents as Cosmetic Ingredients" Cosmetics & Toiletries vol 107, pages 85–94 (November 1992).

Thus, to obtain a further and more sustained elevation of TEML, without inducing excessive irritation, I have discovered that the addition of specific cerebrosides, notably, Types 1 or 2, to the compositions of the invention described above works synergistically to provide the desired results. The designations "1" and "2" can be understood to refer to particular molecular structures by referring to the structures of the corresponding ceramides, see for example Rieger, FIG. 2, page 88.

In skin lipid metabolism, ceramides are produced by acylation of sphingosine and cerebrosides are the products of glycosylation of ceramides. Ceramides and cerebrosides make up a small percentage of skin lipids. Cerebrosides are synthesized and found in the basal cell layers. Here they are converted to ceramides which are found throughout the epidermis. Thus ceramides are found predominantly in the outer epidermal layers of mature cells, including the stratum corneum, while cerebrosides are predominantly found in the inner, basal layers of growing cells.

Sphingosine, a smaller molecule and structural precursor of ceramides and cerebrosides, is found primarily in the basal layers. Sphingosine is also found in significant amounts in desquamated stratum corneum cells, as ceramides are enzymatically degraded during the exfoliation process. When the barrier is impaired, specific signals are released, triggering an activation of epidermal and dermal metabolism. Some of these signals activate the synthesis of new epidermal lipids to repair the barrier and return TEML to normal. This repair turns off signals responsible for activating epidermal and dermal metabolism. The addition of selected cerebrosides (but not ceramides nor sphingosine) interferes with the barrier repair to such a degree that the activation of epidermal and dermal metabolism is maintained over a long period of time resulting in changes which improve the skin's structure.

The barrier repair interference caused by selected cerebrosides is not such as to cause negative surface effects on the external stratum corneum. Rather, the barrier repair inhibition process appears to be an interference with epidermal lipid production which enables activated epidermal and dermal metabolism to be maintained over extended periods of weeks and months. These concepts are verified by the results of clinical experiments reported hereinbelow.

These conclusions and results as to a barrier repair inhibitor role for cerebrosides are quite unexpected since conventional teaching suggests that cerebrosides, like ceramides, phospholipids, cholesterol and other skin lipids, should help repair a defective barrier not hinder the repair.

Alternative Barrier Repair Inhibitors

Pursuant to the invention, it may be postulated that the barrier repair inhibition properties of specific cerebrosides are attributable to an inhibition of ceramide synthesis. The principal lipid "mortar" of the stratum corneum, providing the skin's water or moisture barrier, comprises ceramides, cholesterol and the fatty acids. These components are organized around the phospholipid outer membranes of solid stratum corneum cells into a structure which binds the cells together into a coherent, protective, water-resistant macro-membrane: the skin's outer surface.

Pursuant to this model, the invention contemplates that a shortage of any of these essential lipid barrier constituents may prevent proper rebuilding of the lipid mortar and thus prevent repair of the barrier. Specific cerebrosides disrupt this lipid organization by apparently depriving the mortar of essential ceramide components. The invention contemplates that equivalent or otherwise effective barrier disruption can be achieved in other ways for example by inhibiting production of other essential lipid components, notably cholesterol or the free fatty acids. Anticholesterogenics, or cholesterol synthesis inhibitors, are known and have been developed as therapeutic drugs for controlling hypercholesteremia, for example lovastatin, which is a potent inhibitor of the reductase rate controlling enzyme in cholesterol biosynthesis. Such drugs and equivalent natural compounds are contemplated as being effective barrier repair inhibitors, for the purposes of this invention.

Further Suitable Vehicles

Any cosmetically acceptable vehicles customarily employed for delivering skin treatments can be employed in formulating chemically based barrier disruption treatments pursuant to the practice of this invention, so long as the vehicles used avoid significant quantities of occlusive agents or of barrier repair agents that act to reduce, or inhibit, elevation of TEML levels. If a barrier repair inhibitor, such as a specific cerebroside material is used, inhibition interfering agents such as cholesterol and free fatty acids should also be avoided. Suitable vehicles may be aqueous or hydroalcoholic tonics but preferably do not employ oil or other hydrophobics, unless the oils or other hydrophobics are volatile. Common cosmetic formulations such as creams and lotions employing substantial quantities of oils such as mineral oil are contraindicated. If desired, the vehicle can simply be plain water, although small quantities of alcohol or other organic solvent may be needed to dissolve or disperse the small quantities of any more hydrophobic active ingredients of the invention such as cerebrosides or retinoids, which may be employed by the present invention. Ingredients such as surfactants and hydroxy acids, or their polar equivalents such as keto acids, are readily soluble in water. Other vehicles that will facilitate application of barrier disruption treatments without occluding TEML will be apparent to those skilled in the art.

If desired, the active ingredients can be formulated in a cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol. While a number of lower aliphatic alcohols, both monohydric and polyhydric can be used, ethanol and propanol are the most preferred choices. Cerebrosides are significantly hydrophobic and only poorly, if at all soluble in hydroalcoholic media, so that, depending upon their source and concentration, if cerebrosides are included in the composition, the vehicle may also need to include a solubilizer for the cerebrosides such for example as from about 5 to about 20 percent by weight of ethoxydiglycol to achieve proper dissolution of the cerebroside.

Many additives and supplemental materials are known to the art as being useful for incorporation in such vehicles, for example, glycerine up to about 5 percent, preferably 1 or 2 percent is useful as a humectant to counteract the drying effect of the alcohol and to improve the feel of the tonic. Stabilizers, fragrances and colorants are examples of other such additives.

Other suitable vehicles include a hydrophobic dispersion of from about 5 to about 60 weight percent of a hydrophobic fluid dispersed in an aqueous medium, and include water. Any such hydrophobic fluid should be relatively volatile so as not to be retained in the stratum corneum as a barrier-building component, for example a silicone such as dimethicone.

If desired, pH adjustment to a preferred range, for example, pH 3.5–5.0 for an acidic treatment, can be effected with from 0.1 to 10 weight percent of an alkaline medium, for example aqueous sodium hydroxide, arginine or triethanolamine (TEA), and if desired may also be buffered, for example with from about 0.1 to 10 weight percent, preferably about 1 or 2 percent of a suitable buffers such as a TRIS (trimethylolaminomethane) buffers or phosphate buffer.

Theoretical Considerations Regarding Skin Renewal Processes

As previously stated, the invention is not limited by any particular theory but only by the appended claims. Nevertheless it is believed helpful to attempt to describe a possible mechanism or mechanisms for the phenomena I have discovered relative to the skin and my findings that the structure of deteriorated skin can be improved by simple treatments that disrupt the skin's water barrier. A purpose of such a description is to enable those skilled in the art better to understand the invention and what equivalent and alternative methods and compositions can be used in practicing it.

However, an alternative theory pursuant to the invention, but not intended to limit it, is that the stratum corneum, the horny outer layer of the skin system which incorporates the skin's water barrier, functions as a coherent macro-biological membrane. 10 to 20 distinct layers of cells can be recognized in the stratum corneum. It appears that these layers function cooperatively rather than independently so that the stratum corneum membrane constituted by the cell layers maintains many gradients across itself via the partitioning and restriction of certain ionic species, including calcium and larger molecular weight materials.

It further appears that by chronic disruption of the barrier properties, as described above, the skin's electrical potential is altered (since other gradients chemical or electrochemical may also be altered) and the skin recognizes this disruption as a wound condition; it then begins a repair process.

When the skin is wounded heretofore-undefined signals are released and these signals trigger the synthesis and release of the skin's own endogenous growth and repair factors, such as epithelial growth factor (EGF), cytokines, transforming growth factors, and the like. The activity of these factors results in a repair of the wound. When there is no wound to repair, the result is an improvement in the structure of the tissue, in the case of the treatment objectives of the invention that tissue is aged or otherwise deteriorated skin.

Prior workers have believed that the barrier itself did not mediate any significant skin reconstruction or inflammation processes because application of occlusive agents to the disrupted barrier of the skin did not prevent stimulated skin cell proliferation, or hyperplasia, and inflammation responses. Contrary to the teachings of prior workers, I have found that extended disruption of the barrier of human skin not only stimulates valuable reconstruction processes but, surprisingly, inflammation is not a problem.

It appears that daily use alpha hydroxy acids, as conventionally used for skin renewal stimulation, remove a few layers of the stratum corneum without having significant long term effects on the barrier, as measured, for example, at eight weeks, and that this removal of a few layers signals the basal layer of the epidermis to grow faster. In time, alpha hydroxy acids, used continually, can produce a better, thicker epidermis. There is probably no dermal action and no significant cytokine activity. Cytokines are cellular agents which stimulate mitosis or cleavage of cytoplasm after division of the cellular nucleus. Mitosis is a very complex process which can proceed in many different directions, with different outcomes producing many different kinds of cell. There is a large number of cytokines that have different and specific influences on mitosis.

In contrast to the mild effects of daily use alpha hydroxy acids, a skin peel, for example, as induced by a single, concentrated application of an alpha hydroxy acid, such as 40% glycolic acid or trichloracetic acid temporarily removes the barrier, stimulates non-specific cytokine production and produces significant irritation. This response is comparable to an emergency response to injury.

The novel treatments of the invention occupy ground between the mildness of a daily alpha hydroxy acid treatment and the severe attack on the skin system that is constituted by a skin peel treatment. It appears that the treatments I have described are effective to induce chronic barrier removal either by removing enough stratum corneum layers significantly to elevate TEML or by stripping out from the stratum corneum the natural occlusive lipids that comprise the barrier. This moderately aggressive treatment, in addition to providing conventional alpha hydroxy acid basal layer epidermal growth increases, activates cytokine release, producing significant dermal effects such as fibroblast generation, collagen synthesis and improvement in microvasculature, or blood vessel growth. Surprisingly, inflammatory processes do not appear to be triggered. I postulate that inflammatory processes can be avoided if the elevation of TEML does not exceed about four or five times normal. Cytokines, small-molecule substances that mediate or stimulate cellular or cytoplasmic cleavage, influence many different processes that are relevant to skin and tissue renewal: some cytokines mediate cellular proliferation and differentiation, influencing growth of healthy tissue while many are implicated in defensive immune and inflammatory responses to damage or threats, and some cytokines are implicated in both inflammatory and normal growth processes, as well as, in some cases, immune response functions. There being more than two dozen known cytokines, the biology of their action has a bewildering complexity.

In view of this complexity, that the novel chronic and sustained barrier disruption treatments described herein appear to activate cytokines in a selective manner, favoring cytokines that stimulate skin growth and reconstruction, and avoiding those that cause inflammation and irritation, is surprising. This selectivity is clearly a valuable phenomenon which has been neither taught nor suggested by prior workers.

Prior to my invention it was not known that favorable results could be obtained from disrupting the barrier. It was believed that barrier disruption would, if severe, provoke inflammation and excessive irritation. Elevations of TEML indicative of a disrupted barrier were to be countered by applying an occlusive layer, e.g. petrolatum. It was not known that the barrier could be used to stimulate dermal repair processes. It was believed that such processes were stimulated by injury to the epidermis. I have apparently found that there is a window of stimulation that elicits favorable responses while avoiding unfavorable inflammatory and irritation responses. This window is defined by a chronic and elevated level of TEML which is nevertheless kept below levels associated with complete loss of stratum corneum layers that could be read by the dermal response system as indicative of serious epidermal injury.

Use of Cellulite Treatment Formulations

The formulations employed and preferred for use in the present application are generally less aggressive, or less severe than the treatments disclosed in my parent application for treating cellulite because the treatments herein are intended for general application to any desired skin surface that is deteriorated, including particularly, sensitive facial areas. However, recent teachings, such as those of McCook, suggest that the skin can develop tolerance to alpha hydroxy acids. This being the case and furthermore noting that the relatively severe cellulite treatments disclosed and claimed in the parent application induce surprisingly little irritation, the present invention contemplates that perhaps, after acclimatization with milder treatments, the strong cellulite treatments might be usable on sensitive facial areas. As reported in the parent application, my treatments can induce shrinkage of disordered dermal (rather than epidermal) tissues, which may be of value to tighten sagging or puffy skin. Combination Treatments.

The invention has generally been described in terms of single-stage or homogeneous treatments wherein one or another topical agent or composition is used. Thus, the invention teaches that an adequate level of sustained barrier disruption to obtain the described skin improvement benefits can be obtained by a variety of techniques such as solvent or tape stripping, mechanical abrasion with exfoliants or, in preferred embodiments, by treatment with topical cosmetics containing a suitable combination of active agents, as described.

However, some people may prefer to combine treatments to obtain the benefits of the invention. Thus the teaching herein as to the degree of barrier disruption that is desirable to induce long-term structural skin improvements enables a consumer or professional flexibly to devise an effective treatment program which can comprise a combination of different treatments. Indeed, they may even obtain additional benefits of improved efficacy.

For example, a more complex treatment which might be combined or alternated with other treatments could employ a relatively mild solvent or detergent stripping to remove surface oils, followed by a topical application of a barrier-disruptive gel or cream composition containing an AHA, preferably with a retinoid and preferably also with a cerebroside, within a short time after the solvent stripping, say half an hour or so.

So long as adequate barrier disruption is sustained, such a combined treatment may make possible the use of somewhat less stringent individual treatments, reducing possible side effects such as irritation or drying, or providing quicker or better results, or simply providing a more agreeable treatment. For example solvent stripping with an alcohol/acetone/water system may be less noxious and irritant than acetone, yet provide sufficient stripping of oils, fats and the like to reduce the barrier and improve the effect of an active cream or gel.

Equally, some people may wish to develop a program of treatment which also includes exfoliation with apricot pits or other mechanical means that abrade the skin surface and efficiently remove superficial stratum corneum layers. Other combinations of the described treatments which will provide the benefits of the invention will be apparent to those skilled in the art.

INDUSTRIAL APPLICABILITY

The present invention is particularly suitable for application in the cosmetics and beauty treatment industries to provide new formulations and methods of treatment of deteriorated skin, especially aged skin. Consumers can be provided with new over-the-counter skin-treatment cosmetics that can effect significant structural improvements to damaged or aged skin. Salons can offer a variety of different treatments, or may specialize in one type of treatment suited to the individual client or salon, which treatment or treatments is effected in such manner, as described herein, as to achieve a sustained acute chronic disruption of barrier function, eventually yielding improvements in damaged or deteriorated skin structure.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A skin treatment comprising repeated topical application to structurally deteriorated skin of a skin water-vapor barrier disruption treatment effective to provide chronic disruption of the aged skin's water-vapor barrier said chronic disruption being effective to induce structural improvements in the skin, wherein said treatment comprises topical application to facial or other sensitive areas of the skin of a cosmetic composition comprising, in proportions based on the weight of the composition of:

a) from about 1 to about 6 percent of a cosmetically compatible, pH-reducing hydroxy carboxylic acid to elevate trans-epidermal moisture loss;

b) from about 0.0005 to 0.5 percent of a retinoid cell renewal stimulant; and c) a cerebroside barrier repair inhibitor selected from the group consisting of cerebroside 1, cerebroside 2, and mixtures thereof in a proportion of from about 0.005 to about 1 percent, by weight;

wherein said cosmetic composition is topically applied twice daily for at least eight weeks, whereby the treatment is effective to provide chronic disruption of the aged skin's water-vapor barrier, said chronic disruption being effective to induce structural improvements in the skin and to induce chronic elevated trans-epidermal water vapor loss for a period of from eight weeks until a desired improvement of the aged skin is achieved and said trans-epidermal water vapor loss is elevated by at least one hundred percent after eight weeks of said repeatedly applied treatment.

2. A method of treating skin comprising repeated topical application to deteriorated skin of a skin moisture barrier disruption treatment composition effective to provide acute, chronic disruption of the deteriorated skin's moisture barrier effective to induce structural improvement in the skin, wherein said composition comprises a cerebroside barrier inhibitor selected from the group consisting of cerebroside 1, cerebroside 2, and mixtures thereof in a proportion of from about 0.005 to about 1 percent by weight.

3. A method of treating skin according to claim 2 comprising repeated application of said barrier disruption treatment to facial or other sensitive aged skin areas to induce chronic elevated trans-epidermal water loss for a period of from eight weeks until a desired improvement of the aged skin is achieved.

4. A method according to claim 3 wherein said trans-epidermal water vapor loss is elevated by at least fifty percent after eight weeks of said treatment.

5. A method according to claim 3 continued for at least four further weeks.

6. A method according to claim 3 wherein said treatment is effective to elevate said trans-epidermal water loss by at least one hundred percent and said period of time is from eight to at least twenty-six weeks.

7. A method according to claim 3 wherein said treatment includes topical application of a barrier repair inhibitor to prolong barrier disruption.

8. A method according to claim 3 wherein said treatment is selected from the group consisting of solvent stripping, detergent stripping, tape stripping, mechanical barrier disruption, stratum corneum abrasion and application of chemically active cosmetic agents.

9. A method according to claim 3 comprising topical application to facial or other sensitive areas of the skin of a cosmetic composition comprising, in proportions based on the weight of the composition of:

a) from about 1 to about 5% of a cosmetically compatible, pH-reducing, hydroxy carbocyclic acid to elevate trans-epidermal water vapor loss; and b) from about 0.005 to 0.5% of a retinoid cell renewal stimulant.

10. A method according to claim 9 wherein the cosmetic composition ingredients are present in proportions of from about 2 to about 4 percent of an alpha hydroxy acid, from about 0.01 to about 0.5 percent of a mixture of cerebrosides 1 and 2 and from about 0.1 to about 3.0 percent of a retinyl palmitate.

11. A method according to claim 2 wherein said cosmetic composition is topically applied twice daily for at least eight weeks.

12. A skin treatment composition for daily topical application to structurally deteriorated skin areas, said composition being effective to elevate trans-epidermal moisture loss by at least 100% after 8 weeks of topical application, said treatment comprising, in proportions based on the weight of the composition:

a) a cosmetically compatible, pH-reducing hydroxy carboxylic acid to elevate trans-epidermal moisture loss, in a proportion of from about 1 to about 15%;

b) a retinoid cell renewal stimulant in a proportion of from about 0.005 to about 6.0%;

c) a cerebroside barrier repair inhibitor selected from the group consisting of cerebroside 1, cerebroside 2, and mixtures thereof in a proportion of from about 0.01 to about 5%.

13. A treatment composition according to claim 12 comprising from about 1 to about 6 percent of lactic, glycolic or salicylic acid, or a mixture thereof, from about 0.3 to 3.0 percent of vitamin A palmitate and from about 0.1 to about 0.5 percent of said cerebroside barrier repair inhibitor.

14. A treatment composition according to claim 12 comprising an effective amount of an anti-irritant or an anti-oxidant to control irritation induced by said trans-epidermal moisture loss elevator, and mixtures thereof.

15. A treatment composition for deteriorated skin comprising an effective amount of a water-soluble barrier disruption agent, an effective amount of a lipid-soluble barrier disruption agent and an effective amount of a barrier repair inhibitor selected from the group consisting of cerebroside 1, cerebroside 2 and mixtures there of in a proportion of from about 0.005 to about 1% by weight to inhibit repair of the skin's water barder said amounts being effective to provide chronic sustained barrier disruption sufficient to induce improvement of said deteriorated skin.

16. A treatment composition according to claim 15 comprising, based on the weight of the composition, a proportion of water-soluble barder disruption agent of from about 1 to about 15 percent by weight of the composition.

17. A treatment composition according to claim 15 wherein said water-soluble barrier disruption agent comprises an acid selected from the group consisting of lactic, salicylic and glycolic acid in a proportion of from about 1 to about 6 percent.

18. A treatment composition according to claim 15 wherein said lipid-soluble barrier disruption agent is a retinoid in a proportion of from about 0.1 to about 3.0 percent by weight.

19. A treatment composition according to claim 15 comprising an effective proportion of an anti-irritant or anti-oxidant to control irritation induced by said barrier disruption agents.

20. A treatment composition according to claim 15 comprising from 5 to 10 percent lactic acid, from 0.5 to 4.0 percent vitamin A palmitate and from 0.1 to 0.5 percent of an active cerebroside material.

21. A treatment composition according to claim 15 effective to elevate trans-epidermal moisture loss by at least 50 percent after eight weeks of continual application.

* * * * *

UNITED STATES PATENT AND TRADEMARK OFFICE
CERTIFICATE OF CORRECTION

PATENT NO. : 5,720,963
DATED : February 24, 1998
INVENTOR(S) : Walter P. SMITH

It is certified that error appears in the above-identified patent and that said Letters Patent is hereby corrected as shown below:

In the Claims:

In claim 15, col. 37, line 12, "barder" should read --barrier--.

In claim 15, col. 37, line 17, "barder" should read --barrier--.

Signed and Sealed this

Ninth Day of June, 1998

Attest:

BRUCE LEHMAN

Attesting Officer

Commissioner of Patents and Trademarks